US011800942B2

(12) United States Patent
Milne

(10) Patent No.: US 11,800,942 B2
(45) Date of Patent: Oct. 31, 2023

(54) HEATED BODY PILLOW

(71) Applicant: Sustainable Products Technologies, Conifer, CO (US)

(72) Inventor: Scott William Milne, Conifer, CO (US)

(73) Assignee: Scott William Milne, Conifer, CO (US)

( * ) Notice: Subject to any disclaimer, the term of this patent is extended or adjusted under 35 U.S.C. 154(b) by 0 days.

(21) Appl. No.: 18/047,226

(22) Filed: Oct. 17, 2022

(65) Prior Publication Data

US 2023/0118357 A1 Apr. 20, 2023

Related U.S. Application Data

(60) Provisional application No. 63/256,149, filed on Oct. 15, 2021.

(51) Int. Cl.
*A47G 9/00* (2006.01)
*A47G 9/10* (2006.01)
*G10L 15/22* (2006.01)
*A61B 5/00* (2006.01)

(52) U.S. Cl.
CPC .......... *A47G 9/1036* (2013.01); *A47G 9/007* (2013.01); *A47G 9/1045* (2013.01); *A61B 5/4806* (2013.01); *G10L 15/22* (2013.01); *A47G 2009/006* (2013.01); *A47G 2200/146* (2013.01); *A47G 2200/166* (2013.01); *G10L 2015/223* (2013.01)

(58) Field of Classification Search
CPC .... A47G 9/1036; A47G 9/007; A47G 9/1045; A47G 2009/006; A47G 2200/146; A47G 2200/166; A47G 9/00; A61B 5/4806; G10L 15/22; G10L 2015/223
See application file for complete search history.

(56) References Cited

U.S. PATENT DOCUMENTS

| 10,232,139 | B1* | 3/2019 | Hang | A61M 21/00 |
|---|---|---|---|---|
| 2015/0355605 | A1* | 12/2015 | Franceschetti | A61B 5/024 340/575 |
| 2016/0058652 | A1* | 3/2016 | Reid | A61H 7/007 601/134 |
| 2016/0066716 | A1* | 3/2016 | Rao | A61B 5/6814 600/26 |
| 2016/0327347 | A1* | 11/2016 | Stanley | G05D 23/1919 |
| 2017/0345427 | A1* | 11/2017 | Hardman | G08C 23/04 |

* cited by examiner

*Primary Examiner* — Fredrick C Conley
(74) *Attorney, Agent, or Firm* — Malcolm Pipes

(57) ABSTRACT

Methods, apparatuses, and computer program products for a heated body pillow are described. The pillow may receive, from a user device, one or more commands for adjusting an operating temperature of a heating element located inside an outer covering of the pillow. A power cord coupled to the heating element may be at least partially enclosed by a tubular shroud external to and coupled to the outer covering. The pillow may adjust the operating temperature of the heating element based on receiving the one or more commands.

20 Claims, 14 Drawing Sheets

HEATED BODY PILLOW

CROSS REFERENCE

The present application for patent claims the benefit of U.S. Provisional Patent Application No. 63/256,149 by MILNE, entitled "APPLICATION DRIVEN AUTOMATED BED WARMING BODY PILLOW," filed Oct. 15, 2021, and expressly incorporated by reference herein.

FIELD OF TECHNOLOGY

The present disclosure relates generally to for operating a heated pillow, and more specifically to a heated body pillow.

BACKGROUND

Heating systems are widely deployed in building in various scenarios. However, there is currently a need to reduce carbon combustion and mitigate the effects of climate change. Such heating systems contribute significantly to such carbon combustion and climate change. As such, current methods for heating (including residential use) may be improved.

SUMMARY

The described techniques relate to improved methods, systems, devices, and apparatuses that support a heated body pillow. For example, a heated body pillow may receive, from a user device, one or more commands for adjusting an operating temperature of a heating element located inside an outer covering of the pillow. A power cord coupled to the heating element may be at least partially enclosed by a tubular shroud external to and coupled to the outer covering. The pillow may adjust the operating temperature of the heating element based on receiving the one or more commands.

A method for operating a heated pillow is described. The method may include receiving, from a user device, one or more commands for adjusting an operating temperature of a heating element located inside an outer covering of the pillow, wherein a power cord coupled to the heating element is at least partially enclosed by a tubular shroud external to and coupled to the outer covering and adjusting the operating temperature of the heating element based at least in part on receiving the one or more commands.

An apparatus for operating a heated pillow is described. The apparatus may include a processor, memory coupled with the processor, and instructions stored in the memory. The instructions may be executable by the processor to cause the apparatus to receive, from a user device, one or more commands for adjusting an operating temperature of a heating element located inside an outer covering of the pillow, wherein a power cord coupled to the heating element is at least partially enclosed by a tubular shroud external to and coupled to the outer covering and adjust the operating temperature of the heating element based at least in part on receiving the one or more commands.

Another apparatus for operating a heated pillow is described. The apparatus may include means for receiving, from a user device, one or more commands for adjusting an operating temperature of a heating element located inside an outer covering of the pillow, wherein a power cord coupled to the heating element is at least partially enclosed by a tubular shroud external to and coupled to the outer covering and means for adjusting the operating temperature of the heating element based at least in part on receiving the one or more commands.

A non-transitory computer-readable medium storing code for operating a heated pillow is described. The code may include instructions executable by a processor to receive, from a user device, one or more commands for adjusting an operating temperature of a heating element located inside an outer covering of the pillow, wherein a power cord coupled to the heating element is at least partially enclosed by a tubular shroud external to and coupled to the outer covering and adjust the operating temperature of the heating element based at least in part on receiving the one or more commands.

Some examples of the method, apparatuses, and non-transitory computer-readable medium described herein may further include operations, features, means, or instructions for receiving an indication of an operating temperature of a thermostat associated with a structure and wherein adjusting the operating temperature of the heating element may be based at least in part on receiving the indication of the operating temperature of the thermostat.

Some examples of the method, apparatuses, and non-transitory computer-readable medium described herein may further include operations, features, means, or instructions for transmitting a thermostat temperature adjustment command based at least in part on adjusting the operating temperature of the heating element.

Some examples of the method, apparatuses, and non-transitory computer-readable medium described herein may further include operations, features, means, or instructions for detecting, with a temperature sensor of the pillow, an ambient temperature of an environment in which the pillow may be located and wherein adjusting the operating temperature of the heating element may be based at least in part on the ambient temperature.

Some examples of the method, apparatuses, and non-transitory computer-readable medium described herein may further include operations, features, means, or instructions for transmitting a thermostat temperature adjustment command based at least in part on the ambient temperature of the environment.

Some examples of the method, apparatuses, and non-transitory computer-readable medium described herein may further include operations, features, means, or instructions for receiving the one or more commands comprises receiving a temperature adjustment schedule and adjusting the operating temperature of the heating element comprises adjusting the operating temperature of the heating temperature for a duration of the temperature adjustment schedule in accordance with the temperature adjustment schedule.

In some examples of the method, apparatuses, and non-transitory computer-readable medium described herein, the temperature adjustment schedule indicates that the operating temperature of the heating element may be to be adjusted to a user-designated temperature at least a threshold amount of time before a user-designated point in time.

Some examples of the method, apparatuses, and non-transitory computer-readable medium described herein may further include operations, features, means, or instructions for starting a shutoff timer based at least in part on a shutoff timer command, wherein receiving the one or more commands comprises receiving the shutoff timer command and deactivating the heating element based at least in part on an expiry of the shutoff timer.

Some examples of the method, apparatuses, and non-transitory computer-readable medium described herein may further include operations, features, means, or instructions for receiving, from the user device, one or more second commands for adjusting a second operating temperature of a second heating element located inside an outer covering of the pillow, wherein the power cord may be coupled to the second heating element and adjusting the second operating temperature of the second heating element based at least in part on receiving the one or more second commands.

Some examples of the method, apparatuses, and non-transitory computer-readable medium described herein may further include operations, features, means, or instructions for capturing, via a microphone of the pillow, audio in an environment in which the pillow may be located and transmitting the captured audio to the user device.

Some examples of the method, apparatuses, and non-transitory computer-readable medium described herein may further include operations, features, means, or instructions for capturing, via a microphone of the pillow, audio in an environment in which the pillow may be located, identifying one or more spoken commands in the audio, and transmitting, via a local area network, one or more commands to one or more devices connected to the local area network based at least in part on the one or more spoken commands.

Some examples of the method, apparatuses, and non-transitory computer-readable medium described herein may further include operations, features, means, or instructions for monitoring movement, sound, temperature, or any combination thereof of an environment in which the pillow may be located, determining one or more user sleep events based on the movement, sound, temperature, or any combination thereof, and transmitting, to the user device, a report indicating the one or more user sleep events.

In some examples of the method, apparatuses, and non-transitory computer-readable medium described herein, playing, via a speaker of the pillow, an audible schedule reminder based at least in part on a user-specified event and a time at which the event may be to take place.

Some examples of the method, apparatuses, and non-transitory computer-readable medium described herein may further include operations, features, means, or instructions for receiving, from the user device, an audio recording and playing, via a speaker of the pillow, the audio recording based at least in part on receiving a playback command from the user device.

Some examples of the method, apparatuses, and non-transitory computer-readable medium described herein may further include operations, features, means, or instructions for receiving, from the user device, one or more third commands for adjusting a vibration strength of one or more vibrating elements located inside the outer covering of the pillow, adjusting the vibration strength of the one or more vibrating elements based at least in part on receiving the one or more third commands, and wherein the one or more vibrating elements vibrate in accordance with a user-specified vibration pattern.

In some examples of the method, apparatuses, and non-transitory computer-readable medium described herein, the pillow further comprises a compartment that accepts a flexible, vented case that accepts and secures, at least partially within the case, an aromatic disk, an absorbent material that accepts an aromatic liquid, or both.

Some examples of the method, apparatuses, and non-transitory computer-readable medium described herein may further include operations, features, means, or instructions for receiving, from the user device, one or more fourth commands for adjusting an operating speed of one or more fans coupled to the outer covering, adjusting the operating speed of the one or more fans based at least in part on receiving the one or more fourth commands, and wherein at least a portion of the outer covering may be perforated and the one or more fans direct airflow through the portion of the outer covering.

In some examples of the method, apparatuses, and non-transitory computer-readable medium described herein, at least a portion of the outer covering, at least a portion of the tubular shroud, or both, comprise imitation fur.

DETAILED DESCRIPTION

Figure 1:
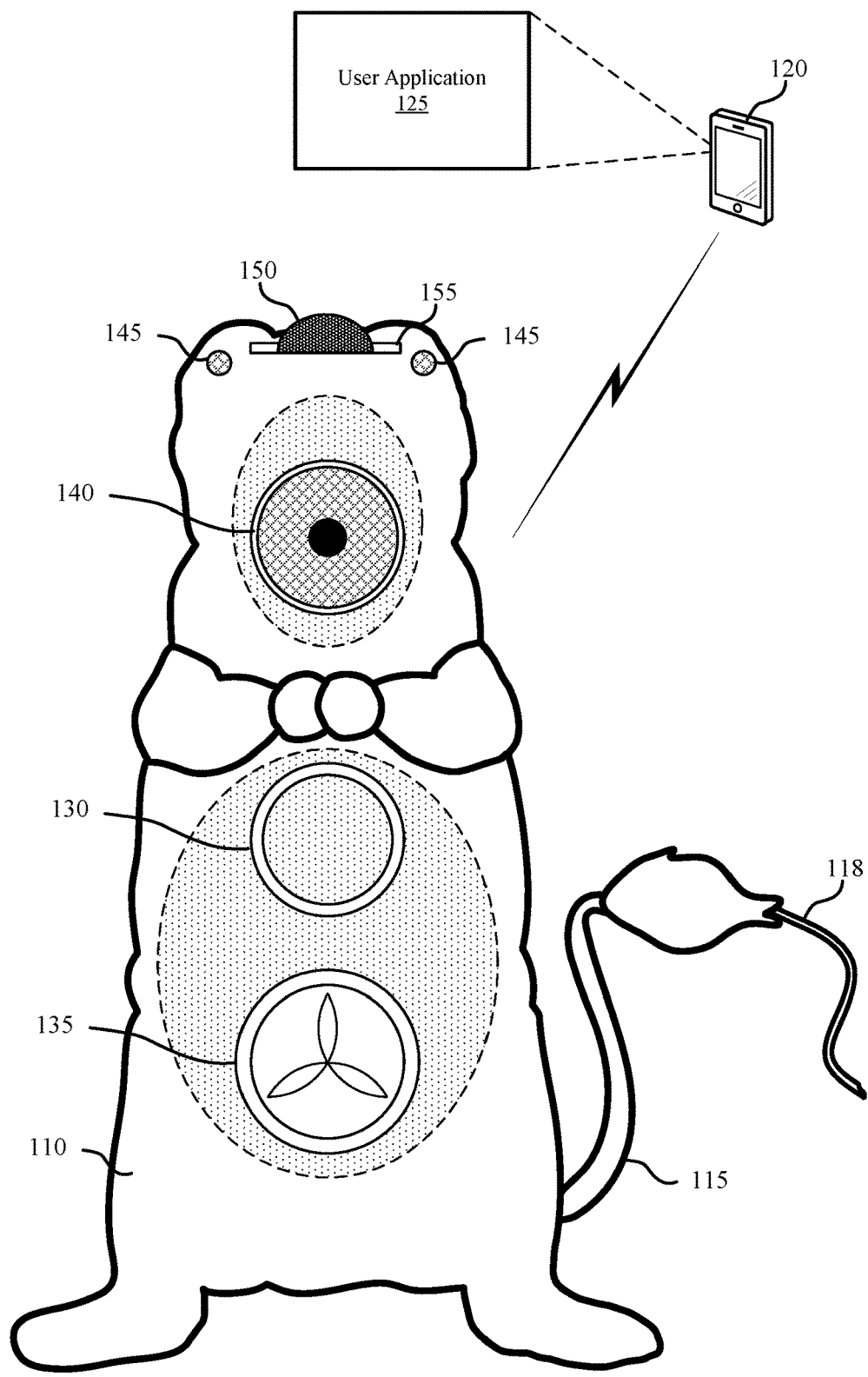
FIG. 1 illustrates an example of a heated body pillow in accordance with examples as disclosed herein.

Reduction of carbon combustion is a priority for many people, companies, and governments. One such avenue of carbon combustion reduction may be found in the residential context. If people were to reduce temperatures of their heating systems (e.g., during the nighttime, while sleeping, etc.), residential energy consumption and, by extension, carbon combustion or other greenhouse gas emissions may be reduced in efforts to mitigate the effects of climate change. However, some people may not be willing to sacrifice comfort for such energy savings or climate change mitigation. As such, an alternative means of maintaining comfort while reducing energy usage and addressing the effects of climate change may be desirable.

As such, a heated body pillow may both provide comfort to the user while allowing the user to lower a thermostat temperature of the user's residence to reduce energy consumption (e.g., since the energy consumed by a heated body pillow may be less than the energy consumed to heat an entire residence). In some examples, the body pillow may include a power cord coupled to a heating element and the power cord may be coupled to a power source to provide electric power to the heating element. The power cord (or a portion thereof) may be partially or completely enclosed by a shroud that may be coupled to an outer covering of the pillow. In some examples, the pillow may include circuitry (e.g., a processor, memory, one or more other elements, or any combination thereof) that may allow one or more aspects, elements, functions, or operations of the pillow to be controlled by a user device. For example, the pillow may receive one or more commands (e.g., from the user device) for activating, deactivating, or adjusting a temperature of the heating element.

In this way, the pillow may provide heating for the user (e.g., in a bed, while the user is sleeping, on a couch, on a recliner, or in another scenario) so that the user may maintain comfort (e.g., a comfortable temperature) while allowing the user to lower the temperature of a building heating system (e.g., a heating system of a house, an apartment, or other residence). For example, the pillow that is heated and controlled as described herein may allow the user to lower the temperature of a heating system that may consume much more energy than the pillow consumes (e.g., since the pillow is only heating the user and the user's close environment, such as a bed as compared to a structure-wide heating system).

Such a pillow may also include one or more additional elements, features, operations, or functions that may further increase the comfort of a user, and some or all such features may be controlled through commands received from the user device (e.g., through an application running on the user device). For example, the pillow may communicate with a thermostat of the heating system or cooling system (e.g., a heating system, a cooling system, or both, of a structure, such as a house or an apartment) to coordinate operation (e.g., when the pillow is heating, an operating temperature of the thermostat of the structure may be automatically reduced, or when the operating temperature of the thermostat is reduced, the pillow may receive a command to activate or adjust a temperature of the heating element of the pillow). Further, the pillow may include a fan or other cooling apparatus that may cool the user, a speaker that may play back audio (e.g., received from the user device), a microphone that may receive commands (e.g., that may be forwarded to one or more other devices), a vibrating element (e.g., a vibrating motor) that may provide a vibration sensation (e.g., for relaxing the user), a pocket or compartment to hold an aromatic element, one or more other features as described herein, or any combination thereof.

Aspects of the disclosure are initially described in the context of an example heated body pillow. Aspects of the disclosure are then described with reference to element diagrams and a process flow. Aspects of the disclosure are further illustrated by and described with reference to apparatus diagrams, system diagrams, and flowcharts that relate to heated body pillow.

It should be appreciated by a person skilled in the art that one or more aspects of the disclosure may be implemented in a pillow 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

FIG. 1 illustrates an example of a pillow 100 in accordance with examples as disclosed herein. Through features of the pillow 100 are described with reference to FIG. 1, one or more other features described herein may be combined or used in any combination with the features described with reference to FIG. 1.

The pillow may include an outer covering 110. In some examples, the outer covering 110 may include one or more features that may resemble features of a person or an animal (e.g., body parts such as arms, legs, feet, a head, a face, a facial feature, one or more other features that resemble a person or animal, or any combination thereof). In some examples, the outer covering 110 may provide a soft or textured feel to the pillow 100. In some examples, at least a portion of the outer covering 110 may include imitation fur (e.g., that may imitate fur of an animal).

The pillow 100 may include the power cord 118 that may provide electrical power to one or more elements of the pillow 100. The pillow 100 may operate on one or more different power sources (e.g., from an outlet of a structure (e.g., 110V or 240V alternating current power), low voltage power such as 5V direct current power provided from a universal serial bus (USB) connection, other low voltage power, or any combination thereof). In some examples, the pillow 100 may include an integrated power supply or may connect to an external power supply (e.g., that includes one or more transformers, regulators, other power supply components, or any combination thereof).

In some examples, the pillow 100 may include the shroud 115 that may enclose at least a portion of the power cord 118. Similar to the outer covering 110, the shroud 115 may include one or more features that may resemble features of a person or an animal. For example, the shroud 115 may resemble a tail of an animal. In some examples, the shroud 115 may include at least a portion that includes imitation fur (e.g., of the same or different type than imitation fur of the outer covering). By providing the shroud 115, the pillow 100 may offer increased comfort to the user by insulating or avoiding contact with the power cord 118.

In some examples, the pillow 100 may communicate with the user device 120. For example the pillow 100 may include a transceiver with which the pillow 100 may communicate with the user device 120 to transmit signaling (e.g., commands or information), receive signaling (e.g., commands or information), or both. In some examples, the power cord 118 may also include one or more connections for communications with the user device 120 (e.g., a USB connection). In some examples, the transceiver may be a wireless transceiver that may communicate with the user device 120 through a wireless local area network (WLAN), a wireless communications system (e.g., a cellular connection), a Bluetooth connection (e.g., a Bluetooth Low Energy connection), one or more other connections, or any combination thereof.

In some examples, the user device 120 may run a user application 125 on the user device 120. The user application 125 may present a user interface to the user for selecting, activating, deactivating, adjusting, or configuring one or more operations, functions, procedures, or elements of the pillow 100.

In some examples, the pillow 100 may include one or more heating elements 130. The heating element 130 may provide heat to the user (e.g., while the user is embracing or sleeping near the pillow) or the environment near the pillow 100 (e.g., for pre-heating the environment, such as a bed, before the user enters the environment). The heating element 130 may operate at different temperatures (e.g., based on one or more received commands from the user device 120). In different examples, the heating element 130 may be located in different locations in the pillow 100. For example, the heating element 130 may be located at a position in a "torso" of a pillow that imitates a human or a creature, simulating the heat produced by a human or animal.

In some examples, the pillow 100 may include multiple heating elements 130. The multiple heating elements 130 may be controlled collectively, in groups, or individually. the user application 125 may include options for the user to control the multiple heating elements 130 to provide heat at different temperatures at different parts of the pillow.

In some examples, the pillow 100 may include one or more fans 135 that may be coupled to the outer covering 110 or may be placed at least partially within the outer covering 110. In some examples, the one or more fans 135 may be located near one or more openings or perforated areas of the outer covering 110 that may allow air to be directed by the fan. In some examples, the pillow 100 may receive one or more commands (e.g., via the user device 120) for adjusting the operation of the fan 135, such as an operating speed, an operating duration, or one or more other parameters. In some examples, the outer covering 110 may include at least a portion that includes a cooling or moisture-wicking fabric or material that may be cool to the touch of the user to increase user comfort while using the device.

In some examples, the pillow 100 may operate based on an operation schedule. Such an operation schedule may define one or more operations of one or more elements of the pillow that should operated at designated times. For example, the operation schedule may include a heating schedule that may define one or more periods of time during which the pillow 100 may activate the heating element 130. Additionally, or alternatively, the operation schedule may indicate a time by which a pre-heating cycle of the pillow 100 is to be completed (e.g., a bedtime). In some examples, the operation schedule may include a shutoff timer or a sleep timer. Such a timer may, upon expiration, deactivate one or more functions of the pillow 100 (e.g., the heating element 130, the fan 135, one or more other elements, or any combination thereof).

In some examples, the pillow 100 may include the speaker 140, one or more microphones 145, a headphone jack, or any combination thereof. Though various functions are described in relation to the speaker 140, the pillow 100 may also operated any of these functions using the headphone jack to transmit audio to headphones worn by the user.

The speaker 140 and the microphones 145 may allow the pillow 100 to operate with one or more audio functions. In some examples, the pillow 100 may operate in a monitoring function (e.g., as a baby monitor) to record ambient sound with the microphones 145 and transmit the recorded audio to the user device 120 (e.g., so that a parent may monitor sounds in the environment in which the pillow 100 is located).

In some examples, the pillow 100 may play back one or more audible reminders (e.g., prerecorded reminders or reminders generated with a text-to-speech process) to a user. The user may program the one or more audible reminders (e.g., calendar events, schedule reminders, meeting reminders, to-do list reminders, etc.) via the user application 125 of the user device 120 or may use a different application (e.g., a calendar application) to provide data for the audible reminders.

In some examples, the pillow 100 may play back an audio recording via the speaker 140 that the user has prerecorded (e.g., with the user device 120, using the user application 125, or using the microphone 145 of the pillow), such as a bedtime story, a message from a family member, a voicemail message stored on or retrieved by the user device 120, music, podcasts, streaming audio, audiobooks, or other audio.

In some examples, the pillow 100 may play back audio at a designated time (e.g., a time designated by the user with the user device 120). The audio may include an alarm sound, music, news, radio, audio from a video, a user-recorded or selected audible indication, or other sound. The playback of the sound may increase in volume or intensity with time or may engage in playback of a pattern of different sound types during a duration of time.

In some examples, the pillow 100 may playback one or more indications of information associated with one or more features of the pillow 100 described herein (e.g., sleep monitoring functions, home alarm functions, configurations or settings for one or more functions such as temperature, heating, cooling, vibrations, etc.). In some examples, the pillow 100 may also receive one or more spoken commands (e.g., via the one or more microphones 145) to adjust one or more parameters of one or more operations of the pillow 100.

In some examples, the pillow 100 may record one or more commands spoken (e.g., based on recognizing a trigger word, phrase, or sound) by a user, translate the audio commands into instructions (e.g., instructions compatible with one or more networked devices) and transmit the instructions to one or more networked devices. For example, the user may configure one or more networked devices (e.g., with the user device 120) to receive the one or more instructions and the user may then issue the spoken command to the pillow 100. The pillow 100 may translate the spoken commands into instructions or may transmit the recorded audio to the user device 120 where the instructions may be generated. In some examples, the pillow 100 may transmit the instructions to the one or more networked devices (e.g., via a WLAN or a Bluetooth connection, for example).

In some examples, the pillow 100 may record audio (e.g., in response to a user trigger, such as a word, phrase, or sound or in response to receiving an indication from the user device 120). Such audio recordings may be for recording thoughts, dreams, reminders, items for a calendar or to-do list, or one or more other recordings. In some examples, the recordings may be stored in a memory of the pillow 100 or may be transmitted to the user device 120 for storage, processing, or transmission (e.g., to networked or cloud storage, optionally associated with a user account).

In some examples, the pillow 100 may include a pocket 155 that receives an aromatic element 150. Additionally, or alternatively, the pocket 155 may be a pouch, opening, compartment, or other containing feature that receives the aromatic element 150. The aromatic element 150 may be a case that may accept an absorbent material (e.g., a sponge) into which the user may deposit an aromatic liquid (e.g., an essential oil, a scent, a perfume, a cologne, etc.). Additionally, or alternatively, the aromatic element 150 may be a material or element that includes or is made of an aromatic material (e.g., an aromatic disk). In some examples, the pocket 155 may include a closure (e.g., a hook-and-loop closure, a button, a zipper, or other closure mechanism) that may aid in retaining the aromatic element 150 in the pocket 155. In some examples, the pocket 155 may include one or more perforations or openings that may allow the aroma from the aromatic element 150 to leave the pocket 155 and be enjoyed by the user. In some examples, the pocket 155 may be located near the fan 135 and the fan 135 may aid in the dispersion of the aroma from the aromatic element 150.

Figure 2:
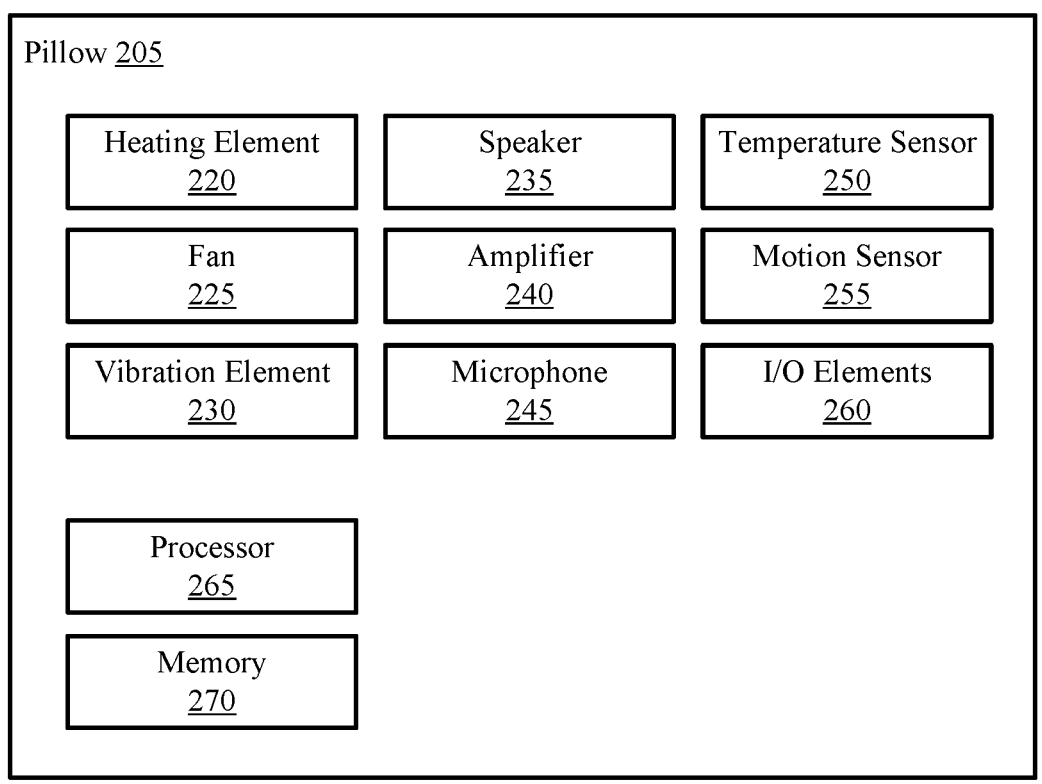
FIG. 2 illustrates an example of a element diagram that supports heated body pillow in accordance with examples as disclosed herein.

FIG. 2 illustrates an example of an element diagram 200 that supports a heated body pillow in accordance with examples as disclosed herein. The element diagram 200 may describe one or more elements of a pillow 205, including the heating element 220, the fan 225, the vibration element 230, the speaker 235, the amplifier 240, the microphone 245, the temperature sensor 250, the motion sensor 255, the input/output (I/O) elements 260, the processor 265, and the memory 270. The pillow 205 may be an example of the pillow 100 describe in relation to FIG. 1. Further, elements of FIG. 2 bearing names similar to elements of other figures may be examples of elements described in other figures.

The pillow 205 may include one or more elements for carrying out one or more of the functions described herein. One or more such elements may perform individual functions, or groups of the elements or all of the elements may operate in concert to perform one or more functions. Though some combinations of elements may be described herein, any combination of the elements may be employed.

In some examples, the pillow 205 may play back audio through the amplifier 240 and the speaker 235 as described herein. In some examples, the pillow 205 may play back audio through the amplifier 240 and direct the amplified signal to a headphone jack to which the user may connect headphones for private listening. Additionally, or alternatively, the pillow 205 may direct the audio to wireless headphones or earphones via the one or more I/O elements 260.

In some examples, the pillow 205 may engage in one or more sleep monitoring operations. For examples, the pillow 205 may monitor sounds (e.g., via the microphone 245) of the environment in which the pillow 205 is located to record one or more events (e.g., a sound exceeding a threshold, such as a decibel threshold, snoring, talking, or one or more other events that, optionally, may be configured via a user application of a user device that is in communication with the pillow 205). Additionally, or alternatively, the pillow 205 may monitor, via the temperature sensor 250, a temperature of the environment in which the pillow 205 is located. Such a temperature may be interpreted to be an ambient temperature, a body temperature of a user, or another temperature. Additionally, or alternatively, the pillow 205 may monitor, via the motion sensor 255, movement occurring in the environment in which the pillow 205 is located. The motion sensor 255 may detect physical movement of the pillow 205 (e.g., via an accelerometer) or may detect physical movement in other ways (e.g., via a camera, an infrared motion sensor, a microwave motion sensor, or other motion sensor). Such movement may be movement of a user using the pillow 205 or may be other movement in the environment in which the pillow 205 is located. Additionally, or alternatively, the pillow 205 may receive one or more indications of measurements from one or more other devices (e.g., the user device).

The pillow 205 may employ such measurements (e.g., sound, temperature, motion, one or more other measurements, or any combination thereof) to determine one or more sleep events occurring in the environment. For example, based on a snoring sound, a temperature measured near the pillow 205, and an amount of movement that a user of the pillow 205 is asleep. Similarly, the pillow 205 may detect speech and an amount of movement exceeding a threshold and may determine that the user has woken up. The pillow 205 may record such measurements, determine such sleep events, and store or transmit indications of such sleep events to another device (e.g., the user device) for storage, viewing, analysis, or further transmission.

In some examples, the pillow 205 may adjust one or more parameters of one or more elements of the pillow 205 based on the one or more measurements, the one or more sleep events, or both, and may do so based on a user configuration. For example, the pillow 205 may adjust an operating temperature of the heating element 220 after detecting a level of movement that is above a threshold indicated in the user configuration, which may be interpreted as an adverse sleep event that may be counteracted by the adjustment of the operating temperature, for example.

In some examples, the pillow 205 may include a vibration element 230 that may vibrate in a pleasing way for the user. For example, the user may use the user application to transmit a command to the pillow 205 to activate the vibration element 230, and the pillow 205 may, in turn, activate the vibration element 230. In some examples, the vibration element 230 may operate at different vibration strengths (e.g., depending on a configuration set by the user) or with different vibration patterns (e.g. a pulsing pattern, a pattern that simulates a heartbeat, a user-defined pattern, or other pattern). The pillow 205 may include multiple vibration elements 230 to provide vibration sensations to different parts of a user's body and different vibration patterns, strengths, or both may be applied to the multiple vibration elements 230.

In some examples, the pillow 205 may include the I/O elements 260. The I/O elements 260 may include one or more elements that allow the pillow 205 to communicate with one or more other devices (e.g. the user device, one or more networked devices, one or more other devices, or any combination thereof).

In some examples, the pillow 205 may include a processor 265 and memory 270 that may carry out one or more functions of the pillow 205 as described herein.

Figure 3:
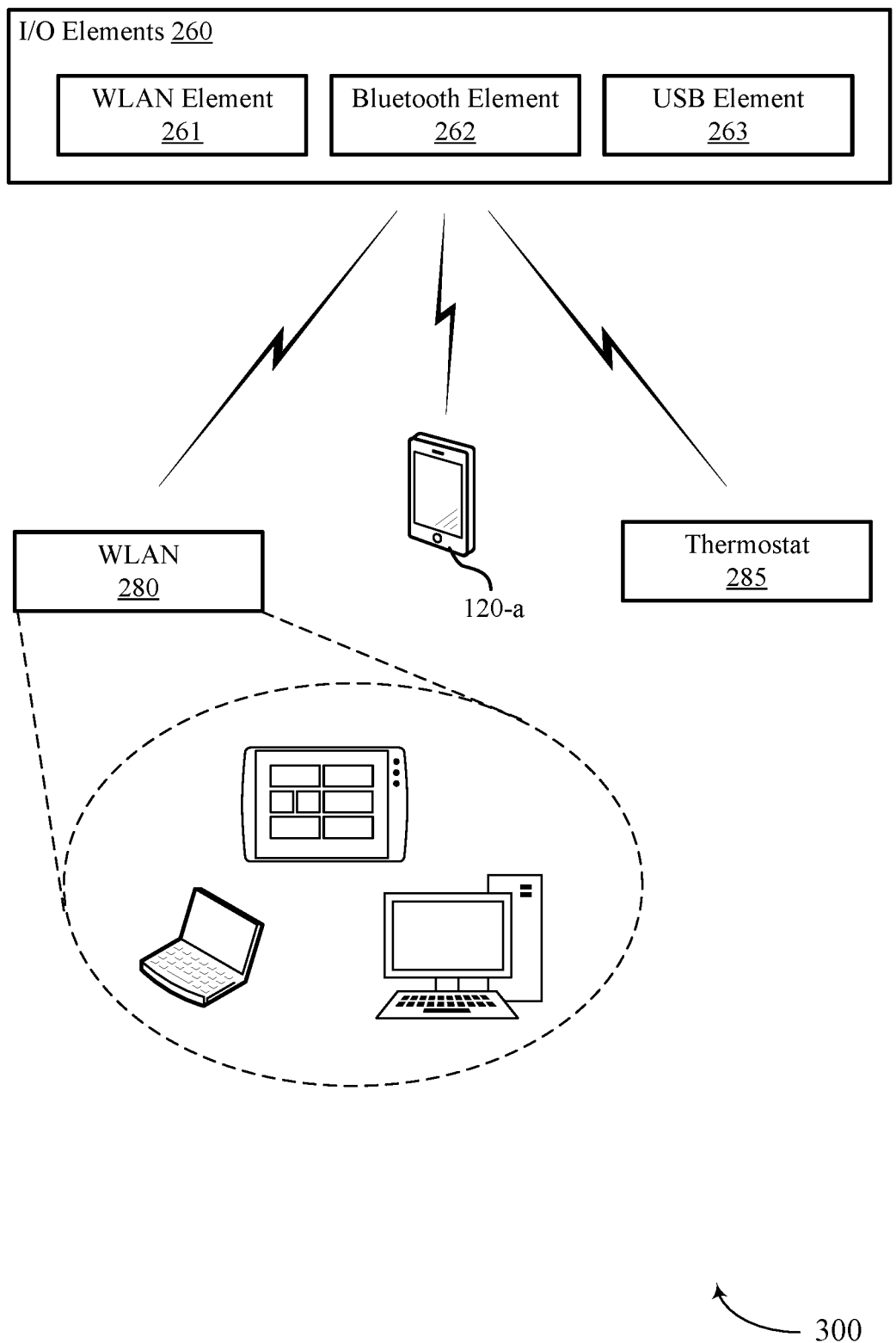
FIG. 3 illustrates an example of a element diagram that supports heated body pillow in accordance with examples as disclosed herein.

FIG. 3 illustrates an example of an element diagram 300 that supports a heated body pillow in accordance with examples as disclosed herein. The element diagram 300 may depict one or more elements of the pillow. For example, the element diagram 300 depicts the I/O elements 260 that may include the WLAN element 261, the Bluetooth element 262, and the USB element 263. Though these examples of I/O elements 260 are described herein, other I/O elements may also be used to carry out the functions described herein.

In some examples, the pillow may communicate with one or more devices via the I/O elements 260. For example, the pillow 205 may communicate with a WLAN 280 via the WLAN element 261. The WLAN 280 may include or be associated with one or more networked devices. As described herein, the pillow may communicate with the one or more networked devices. For example, the pillow may receive one or more spoken commands and may transmit one or more commands or instructions to the one or more networked devices based on the one or more spoken commands. Similarly, the one or more networked devices may transmit one or more commands to the pillow over the WLAN 280 and the pillow may respond by performing one or more actions or functions described herein in response to the received one or more commands. Such networked devices may include speakers, tablets, smart home devices, appliances, the user device 120-a or one or more other devices.

For example, a networked device may be a device associated with an alarm system of a home. The pillow may receive a command from a user (e.g., a spoken command or a command from the user device 120-a) to activate the alarm system. The pillow may transmit a command to the alarm system instructing the alarm system to arm the alarm system. Additionally, or alternatively, the alarm system may transmit an indication that an event that may trigger the alarm (e.g. an opened door or broken window) has been detected and that the pillow is to play back an alarm sound or message informing the user that the alarm has been activated.

In some examples, the pillow may communicate with one or more devices via the Bluetooth element 262. For example, the pillow may communicate with the user device 120-a using the Bluetooth element 262. The user device 120-a may transmit one or more commands to the pillow and the pillow may, in response, perform one or more actions or functions described herein. In another example, the pillow may communicate with wireless earphones of the user using the Bluetooth element 262. The pillow may transmit audio (e.g., an alarm, audible reminders, one or more audio playback examples described herein, other audio, or any combination thereof) via the Bluetooth element 262 to the wireless earphones. Similarly, the pillow may receive audio from the wireless earphones using the Bluetooth element 262.

In some examples, the pillow may communicate with one or more devices via the USB element 263. For example, the user device 120-a may be connected to the pillow using the USB element 263. The USB element 263 may provide a communications link between the pillow and the user device 120-a and may also provide a method of charging battery of the user devices 120-a. In some examples, the pillow may not communicate via the USB element 263 but may still provide power to the user device 120-a for charging the battery of the user device 120-a or for operation of the user device 120-a.

In some examples, the pillow may communicate with a thermostat 285 of a house, apartment, or other dwelling. For example, the pillow may receive an indication of a thermostat 285 configuration (e.g., an operating temperature) and may adjust an operating temperature of the pillow based on the thermostat 285 configuration (e.g., the pillow's heating element may be activated or a temperature thereof increased based on the temperature setting of the thermostat 285). Additionally, or alternatively, the pillow may transmit a command to the thermostat 285 indicating that the thermostat 285 is to adjust the thermostat 285 configuration (e.g., adjust a schedule, adjust a target temperature, or adjust an operating temperature) based on activation of the heating element of the pillow or adjustment of the temperature of the pillow (e.g., after the pillow's heating element is activated, the pillow may transmit a command to the thermostat 285 to lower the temperature of the heating system associated with the thermostat 285). In some examples, the pillow may adjust an operating temperature of the heating element of the pillow based on a temperature detected by the thermostat 285. Additionally, or alternatively, the pillow may employ the use of a temperature sensor that detects a temperature in an environment in which the pillow is located and may adjust a parameter (e.g., a target temperature) of the thermostat 285 based on the detected temperature.

Figure 4:
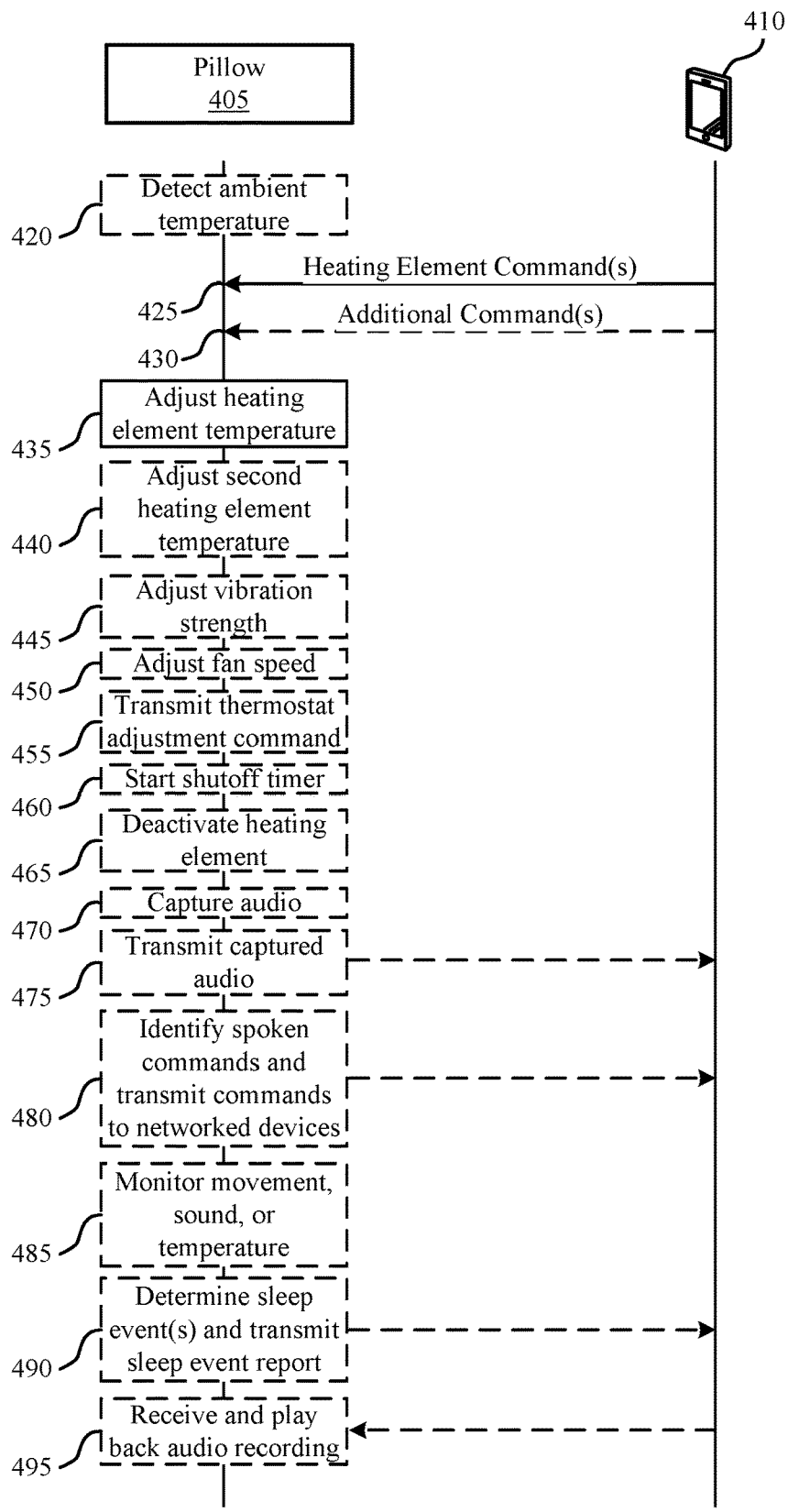
FIG. 4 illustrates an example of a process flow that supports heated body pillow in accordance with examples as disclosed herein.

FIG. 4 illustrates an example of a process flow 400 that supports a pillow 405 in accordance with examples as disclosed herein. The process flow 400 may implement various aspects of the present disclosure described herein. The elements described in the process flow 400 (e.g., the pillow 405 may be examples of similarly-named elements described herein.

In the following description of the process flow 400, the operations between the various entities or elements may be performed in different orders or at different times. Some operations may also be left out of the process flow 400, or other operations may be added. Although the various entities or elements are shown performing the operations of the process flow 400, some aspects of some operations may also be performed by other entities or elements of the process flow 400 or by entities or elements that are not depicted in the process flow, or any combination thereof.

At 420, the pillow 405 may detect, with a temperature sensor of the pillow 405, an ambient temperature of an environment in which the pillow 405 is located.

At 425, the pillow 405 may receive, from a user device 410, one or more commands for adjusting an operating temperature of a heating element located inside an outer covering of the pillow 405 and a power cord coupled to the heating element is at least partially enclosed by a tubular shroud external to and coupled to the outer covering.

In some examples, the pillow 405 further may include a compartment that accepts a flexible, vented case that accepts and secures, at least partially within the case, an aromatic disk, an absorbent material that accepts an aromatic liquid, or both. In some examples, at least a portion of the outer covering, at least a portion of the tubular shroud, or both, comprise imitation fur.

In some examples, receiving the one or more commands may include receiving a temperature adjustment schedule. In some examples, the temperature adjustment schedule may indicate that the operating temperature of the heating element is to be adjusted to a user-designated temperature at least a threshold amount of time before a user-designated point in time.

In some examples, receiving the one or more commands may include receiving a shutoff timer command.

At 430, the pillow 405 may receive, from the user device 410, one or more second commands for adjusting a second operating temperature of a second heating element located inside an outer covering of the pillow 405 and the power cord is coupled to the second heating element. Additionally, or alternatively, the pillow 405 may receive, from the user device 410, one or more third commands for adjusting a vibration strength of one or more vibrating elements located inside the outer covering of the pillow 405. Additionally, or alternatively, the pillow 405 may receive, from the user device 410, one or more fourth commands for adjusting an operating speed of one or more fans coupled to the outer covering. Additionally, or alternatively, the pillow 405 may receive an indication of an operating temperature of a thermostat associated with a structure.

At 435, the pillow 405 may adjust the operating temperature of the heating element based on receiving the one or more commands.

In some examples, adjusting the operating temperature of the heating element is based on receiving the indication of the operating temperature of the thermostat. In some examples, adjusting the operating temperature of the heating element is based on the ambient temperature.

In some examples, adjusting the operating temperature of the heating element may include adjusting the operating temperature of the heating temperature for a duration of the temperature adjustment schedule in accordance with the temperature adjustment schedule.

At 440, the pillow 405 may adjust the second operating temperature of the second heating element based on receiving the one or more second commands.

At 445, the pillow 405 may adjust the vibration strength of the one or more vibrating elements based on receiving the one or more third commands. In some examples, the one or more vibrating elements vibrate in accordance with a user-specified vibration pattern.

At 450, the pillow 405 may adjust the operating speed of the one or more fans based on receiving the one or more third commands. In some examples, at least a portion of the outer covering is perforated and the one or more fans direct airflow through the portion of the outer covering.

At 455, the pillow 405 may transmit a thermostat temperature adjustment command based on adjusting the operating temperature of the heating element. Additionally, or alternatively, the pillow 405 may transmit a thermostat temperature adjustment command based on the ambient temperature of the environment.

At 460, the pillow 405 may start a shutoff timer based on the shutoff timer command.

At 465, the pillow 405 may deactivate the heating element based on an expiry of the shutoff timer At 470, the pillow 405 may capture, via a microphone of the pillow 405, audio in an environment in which the pillow 405 is located.

At 475, the pillow 405 may transmit the captured audio to the user device 410.

At 480, the pillow 405 may identify one or more spoken commands in the audio. Additionally, or alternatively, the pillow 405 may transmit, via a local area network, one or more commands to one or more devices connected to the local area network based on the one or more spoken commands.

At 485, the pillow 405 may monitor, movement, sound, temperature, or any combination thereof of an environment in which the pillow 405 is located.

At 490, the pillow 405 may determine one or more user sleep events based on the movement, sound, temperature, or any combination thereof. Additionally, or alternatively, the pillow 405 may transmit, to the user device 410, a report indicating the one or more user sleep events.

At 495, the pillow 405 may receive, from the user device 410, an audio recording. Additionally, or alternatively, the pillow 405 may play, via a speaker of the pillow 405, an audible schedule reminder based on a user-specified event and a time at which the event is to take place. Additionally, or alternatively, the pillow 405 may play, via the speaker of the pillow 405, the audio recording based on receiving a playback command from the user device 410.

Figure 5:
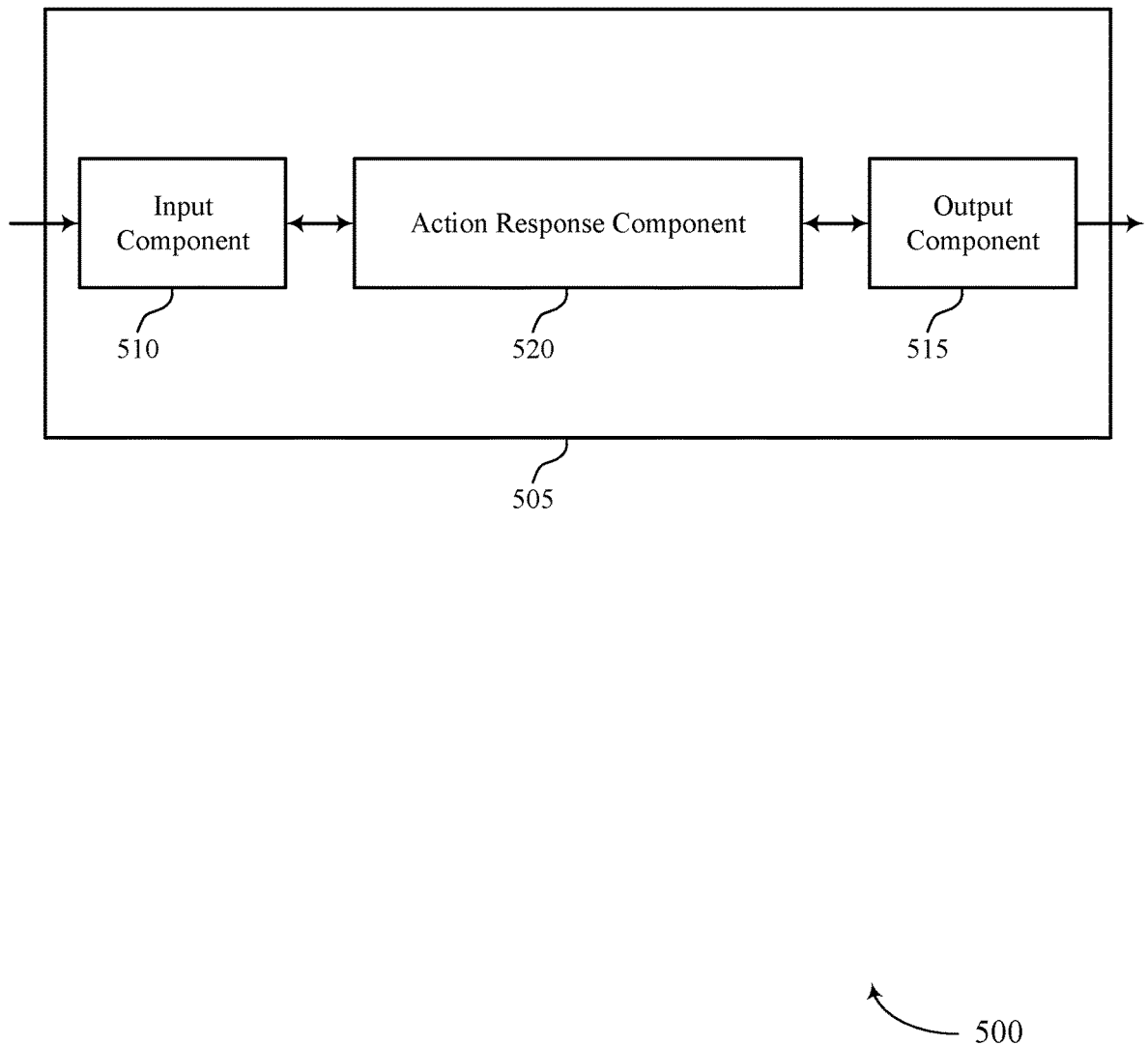
FIGS. 5 and 6 illustrate block diagrams of devices that support a heated body pillow in accordance with examples as disclosed herein.

FIG. 5 illustrates a block diagram 500 of a device 505 that supports a heated body pillow in accordance with examples as disclosed herein. The device 505 may be an example of aspects of a Body Pillow as described herein. The device 505 may include an input component 510, an output component 515, and an action response component 520. The device 505 may also include a processor. Each of these components may be in communication with one another (e.g., via one or more buses).

The input component 510 may manage input signals for the device 505. For example, the input component 510 may identify input signals based on an interaction with a modem, a keyboard, a mouse, a touchscreen, a user device (e.g., over one or more wired or wireless connections), or a similar device. These input signals may be associated with user input or processing at other components or devices. In some cases, the input component 510 may utilize an operating system such as iOS®, ANDROID®, MS-DOS®, MS-WINDOWS®, OS/2®, UNIX®, LINUX®, or another known operating system to handle input signals. The input component 510 may send aspects of these input signals to other components of the device 505 for processing. For example, the input component 510 may transmit input signals to the action response component 520 to support a heated body pillow. In some cases, the input component 510 may be a component of an I/O controller 810 as described with reference to FIG. 8.

The output component 515 may manage output signals for the device 505. For example, the output component 515 may receive signals from other components of the device 505, such as the action response component 520, and may transmit these signals to other components or devices (e.g., the user device). In some specific examples, the output component 515 may transmit output signals for display in a user interface, for storage in a database or data store, for further processing at a server or server cluster, or for any other processes at any number of devices or systems. In some cases, the output component 515 may be a component of an I/O controller 810 as described with reference to FIG. 8.

The action response component 520, the input component 510, the output component 515, or various combinations thereof or various components thereof may be examples of means for performing various aspects of heated body pillow as described herein. For example, the action response component 520, the input component 510, the output component 515, or various combinations or components thereof may support a method for performing one or more of the functions described herein.

In some examples, the action response component 520, the input component 510, the output component 515, or various combinations or components thereof may be implemented in hardware (e.g., in communications management circuitry). The hardware may include a processor, a DSP, an ASIC, an FPGA or other programmable logic device, a discrete gate or transistor logic, discrete hardware components, or any combination thereof configured as or otherwise supporting a means for performing the functions described in the present disclosure. In some examples, a processor and memory coupled with the processor may be configured to perform one or more of the functions described herein (e.g., by executing, by the processor, instructions stored in the memory).

Additionally, or alternatively, in some examples, the action response component 520, the input component 510, the output component 515, or various combinations or components thereof may be implemented in code (e.g., as communications management software or firmware) executed by a processor. If implemented in code executed by a processor, the functions of the action response component 520, the input component 510, the output component 515, or various combinations or components thereof may be performed by a general-purpose processor, a DSP, a CPU, an ASIC, an FPGA, or any combination of these or other programmable logic devices (e.g., configured as or otherwise supporting a means for performing the functions described in the present disclosure).

In some examples, the action response component 520 may be configured to perform various operations (e.g., receiving, monitoring, transmitting) using or otherwise in cooperation with the input component 510, the output component 515, or both. For example, the action response component 520 may receive information from the input component 510, send information to the output component 515, or be integrated in combination with the input component 510, the output component 515, or both to receive information, transmit information, or perform various other operations as described herein.

The action response component 520 may support operating a heated pillow in accordance with examples as disclosed herein. For example, the action response component 520 may be configured as or otherwise support a means for receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The action response component 520 may be configured as or otherwise support a means for adjusting the operating temperature of the heating element based at least in part on receiving the one or more commands.

By including or configuring the action response component 520 in accordance with examples as described herein, the device 505 (e.g., a processor controlling or otherwise coupled with the input component 510, the output component 515, the action response component 520, or a combination thereof) may support techniques for [[*Add modem/processor level advantages (e.g., reduced processing, reduced power consumption, more efficient utilization of communication resources)*]]

Figure 6:
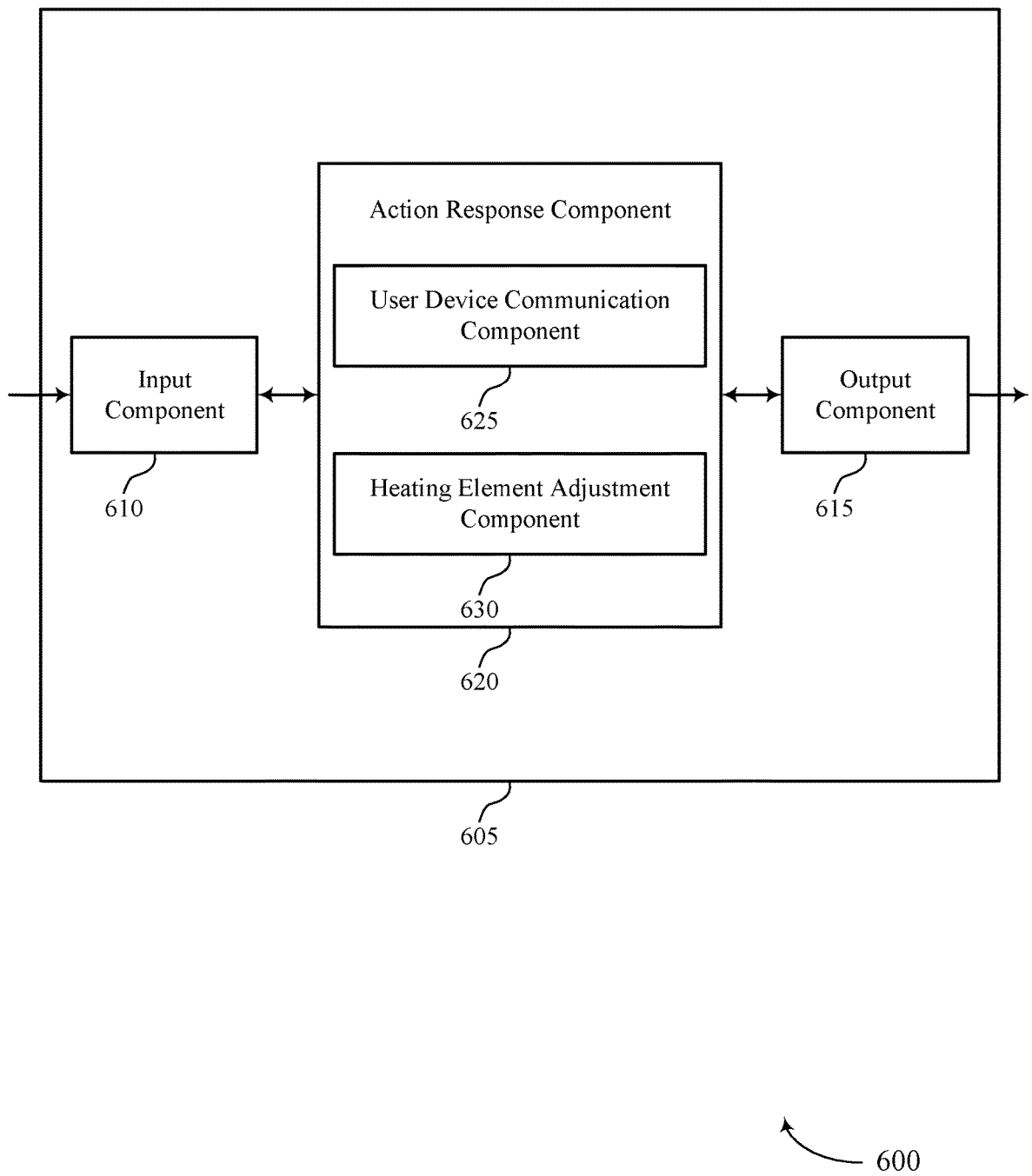

FIG. 6 illustrates a block diagram 600 of a device 605 that supports a heated body pillow in accordance with examples as disclosed herein. The device 605 may be an example of aspects of a device 505 or a Body Pillow 115 as described herein. The device 605 may include an input component 610, an output component 615, and an action response component 620. The device 605 may also include a processor. Each of these components may be in communication with one another (e.g., via one or more buses).

The input component 610 may manage input signals for the device 605. For example, the input component 610 may identify input signals based on an interaction with a modem, a keyboard, a mouse, a touchscreen, or a similar device. These input signals may be associated with user input or processing at other components or devices. In some cases, the input component 610 may utilize an operating system such as iOS®, ANDROID®, MS-DOS®, MS-WINDOWS®, OS/2®, UNIX®, LINUX®, or another known operating system to handle input signals. The input component 610 may send aspects of these input signals to other components of the device 605 for processing. For example, the input component 610 may transmit input signals to the action response component 620 to support a heated body pillow. In some cases, the input component 610 may be a component of an I/O controller 810 as described with reference to FIG. 8.

The output component 615 may manage output signals for the device 605. For example, the output component 615 may receive signals from other components of the device 605, such as the action response component 620, and may transmit these signals to other components or devices. In some specific examples, the output component 615 may transmit output signals for display in a user interface, for storage in a database or data store, for further processing at a server or server cluster, or for any other processes at any number of devices or systems. In some cases, the output component 615 may be a component of an I/O controller 810 as described with reference to FIG. 8.

The device 605, or various components thereof, may be an example of means for performing various aspects of heated body pillow as described herein. For example, the action response component 620 may include a user device communication component 625 a heating element adjustment component 630, or any combination thereof. The action response component 620 may be an example of aspects of a action response component 520 as described herein. In some examples, the action response component 620, or various components thereof, may be configured to perform various operations (e.g., receiving, monitoring, transmitting) using or otherwise in cooperation with the input component 610, the output component 615, or both. For example, the action response component 620 may receive information from the input component 610, send information to the output component 615, or be integrated in combination with the input component 610, the output component 615, or both to receive information, transmit information, or perform various other operations as described herein.

The action response component 620 may support operating a heated pillow in accordance with examples as disclosed herein. The user device communication component 625 may be configured as or otherwise support a means for receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The heating element adjustment component 630 may be configured as or otherwise support a means for adjusting the operating temperature of the heating element based at least in part on receiving the one or more commands.

Figure 7:
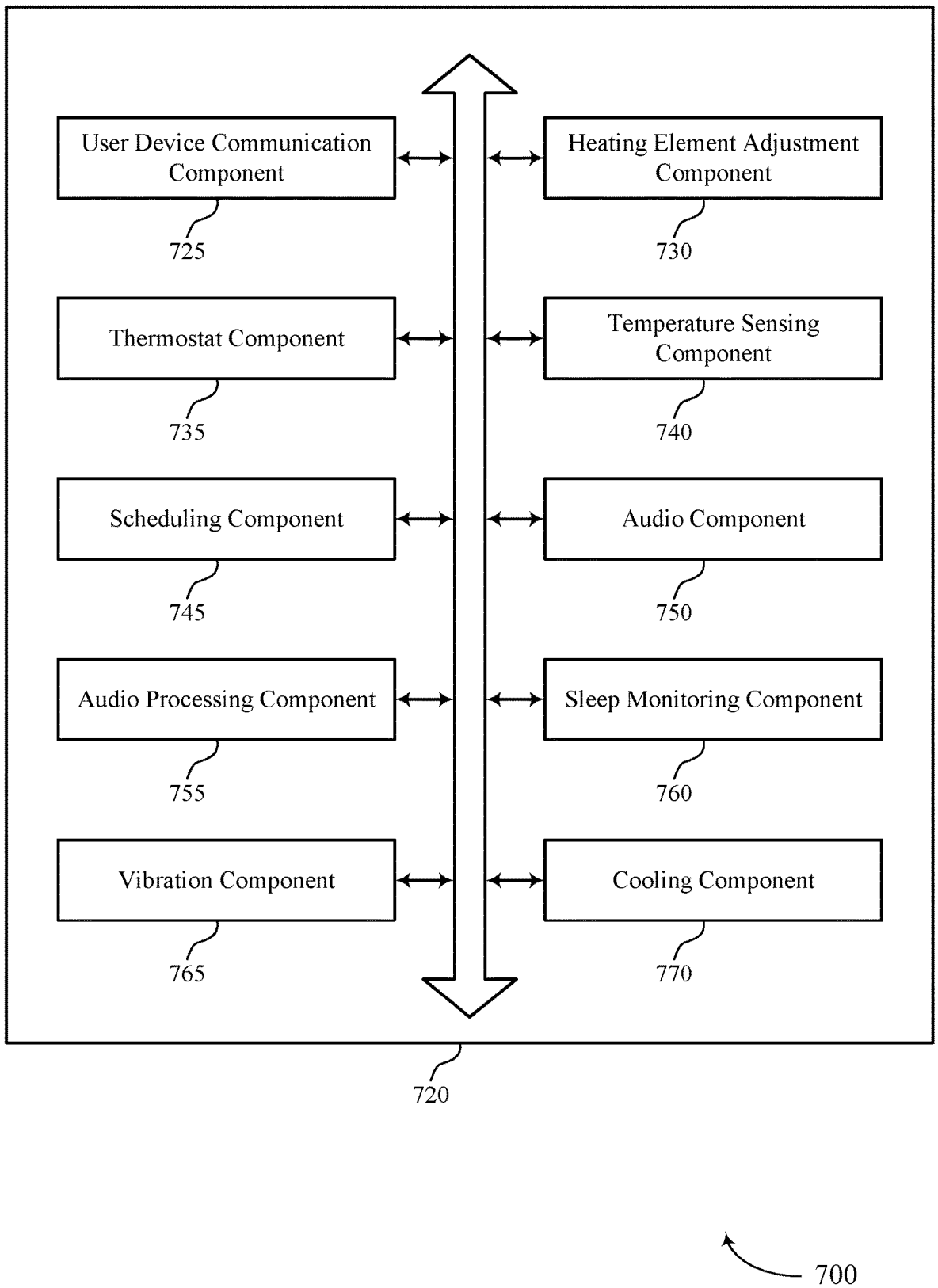
FIG. 7 illustrates a block diagram of an action response component that supports a heated body pillow in accordance with examples as disclosed herein.

FIG. 7 illustrates a block diagram 700 of an action response component 720 that supports a heated body pillow in accordance with examples as disclosed herein. The action response component 720 may be an example of aspects of an action response component 520, an action response component 620, or both, as described herein. The action response component 720, or various components thereof, may be an example of means for performing various aspects of heated body pillow as described herein. For example, the action response component 720 may include a user device communication component 725, a heating element adjustment component 730, a thermostat component 735, a temperature sensing component 740, a scheduling component 745, an audio component 750, an audio processing component 755, a sleep monitoring component 760, a vibration component 765, a cooling component 770, or any combination thereof. Each of these components may communicate, directly or indirectly, with one another (e.g., via one or more buses).

The action response component 720 may support operating a heated pillow in accordance with examples as disclosed herein. The user device communication component 725 may be configured as or otherwise support a means for receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The heating element adjustment component 730 may be configured as or otherwise support a means for adjusting the operating temperature of the heating element based at least in part on receiving the one or more commands.

In some examples, the thermostat component 735 may be configured as or otherwise support a means for receiving an indication of an operating temperature of a thermostat associated with a structure. In some examples, the heating element adjustment component 730 may be configured as or otherwise support a means for wherein adjusting the operating temperature of the heating element is based at least in part on receiving the indication of the operating temperature of the thermostat.

In some examples, the thermostat component 735 may be configured as or otherwise support a means for transmitting a thermostat temperature adjustment command based at least in part on adjusting the operating temperature of the heating element.

In some examples, the temperature sensing component 740 may be configured as or otherwise support a means for detecting, with a temperature sensor of the heated pillow, an ambient temperature of an environment in which the pillow is located. In some examples, the heating element adjustment component 730 may be configured as or otherwise support a means for wherein adjusting the operating temperature of the heating element is based at least in part on the ambient temperature.

In some examples, the thermostat component 735 may be configured as or otherwise support a means for transmitting a thermostat temperature adjustment command based at least in part on the ambient temperature of the environment.

In some examples, receiving the one or more commands comprises receiving a temperature adjustment schedule. In some examples, adjusting the operating temperature of the heating element comprises adjusting the operating temperature of the heating temperature for a duration of the temperature adjustment schedule in accordance with the temperature adjustment schedule.

In some examples, the temperature adjustment schedule indicates that the operating temperature of the heating element is to be adjusted to a user-designated temperature at least a threshold amount of time before a user-designated point in time.

In some examples, the scheduling component 745 may be configured as or otherwise support a means for starting a shutoff timer based at least in part on a shutoff timer command, wherein receiving the one or more commands comprises receiving the shutoff timer command. In some examples, the heating element adjustment component 730 may be configured as or otherwise support a means for deactivating the heating element based at least in part on an expiry of the shutoff timer.

In some examples, the user device communication component 725 may be configured as or otherwise support a means for receiving, from the user device, one or more second commands for adjusting a second operating temperature of a second heating element located inside an outer covering of the pillow, wherein the power cord is coupled to the second heating element. In some examples, the heating element adjustment component 730 may be configured as or otherwise support a means for adjusting the second operating temperature of the second heating element based at least in part on receiving the one or more second commands.

In some examples, the audio component 750 may be configured as or otherwise support a means for capturing, via a microphone of the pillow, audio in an environment in which the pillow is located. In some examples, the user device communication component 725 may be configured as or otherwise support a means for transmitting the captured audio to the user device.

In some examples, the audio component 750 may be configured as or otherwise support a means for capturing, via a microphone of the pillow, audio in an environment in which the pillow is located. In some examples, the audio processing component 755 may be configured as or otherwise support a means for identifying one or more spoken commands in the audio. In some examples, the user device communication component 725 may be configured as or otherwise support a means for transmitting, via a local area network, one or more commands to one or more devices connected to the local area network based at least in part on the one or more spoken commands.

In some examples, the sleep monitoring component 760 may be configured as or otherwise support a means for monitoring movement, sound, temperature, or any combination thereof of an environment in which the pillow is located. In some examples, the sleep monitoring component 760 may be configured as or otherwise support a means for determining one or more user sleep events based on the movement, sound, temperature, or any combination thereof. In some examples, the user device communication component 725 may be configured as or otherwise support a means for transmitting, to a user device, a report indicating the one or more user sleep events.

In some examples, the audio component 750 may be configured as or otherwise support a means for playing, via a speaker of the pillow, an audible schedule reminder based at least in part on a user-specified event and a time at which the event is to take place.

In some examples, the user device communication component 725 may be configured as or otherwise support a means for receiving, from a user device, an audio recording. In some examples, the audio component 750 may be configured as or otherwise support a means for playing, via a speaker of the pillow, the audio recording based at least in part on receiving a playback command from the user device.

In some examples, the user device communication component 725 may be configured as or otherwise support a means for receiving, from the user device, one or more third commands for adjusting a vibration strength of one or more vibrating elements located inside the outer covering of the pillow. In some examples, the vibration component 765 may be configured as or otherwise support a means for adjusting the vibration strength of the one or more vibrating elements based at least in part on receiving the one or more third commands. In some examples, the vibration component 765 may be configured as or otherwise support a means for wherein the one or more vibrating elements vibrate in accordance with a user-specified vibration pattern.

In some examples, the pillow further comprises a compartment that accepts a flexible, vented case that accepts and secures, at least partially within the case, an aromatic disk, an absorbent material that accepts an aromatic liquid, or both.

In some examples, the user device communication component 725 may be configured as or otherwise support a means for receiving, from the user device, one or more fourth commands for adjusting an operating speed of one or more fans coupled to the outer covering. In some examples, the cooling component 770 may be configured as or otherwise support a means for adjusting the operating speed of the one or more fans based at least in part on receiving the one or more fourth commands. In some examples, the cooling component 770 may be configured as or otherwise support a means for wherein at least a portion of the outer covering is perforated and the one or more fans direct airflow through the portion of the outer covering.

In some examples, at least a portion of the outer covering, at least a portion of the tubular shroud, or both, comprise imitation fur.

Figure 8:
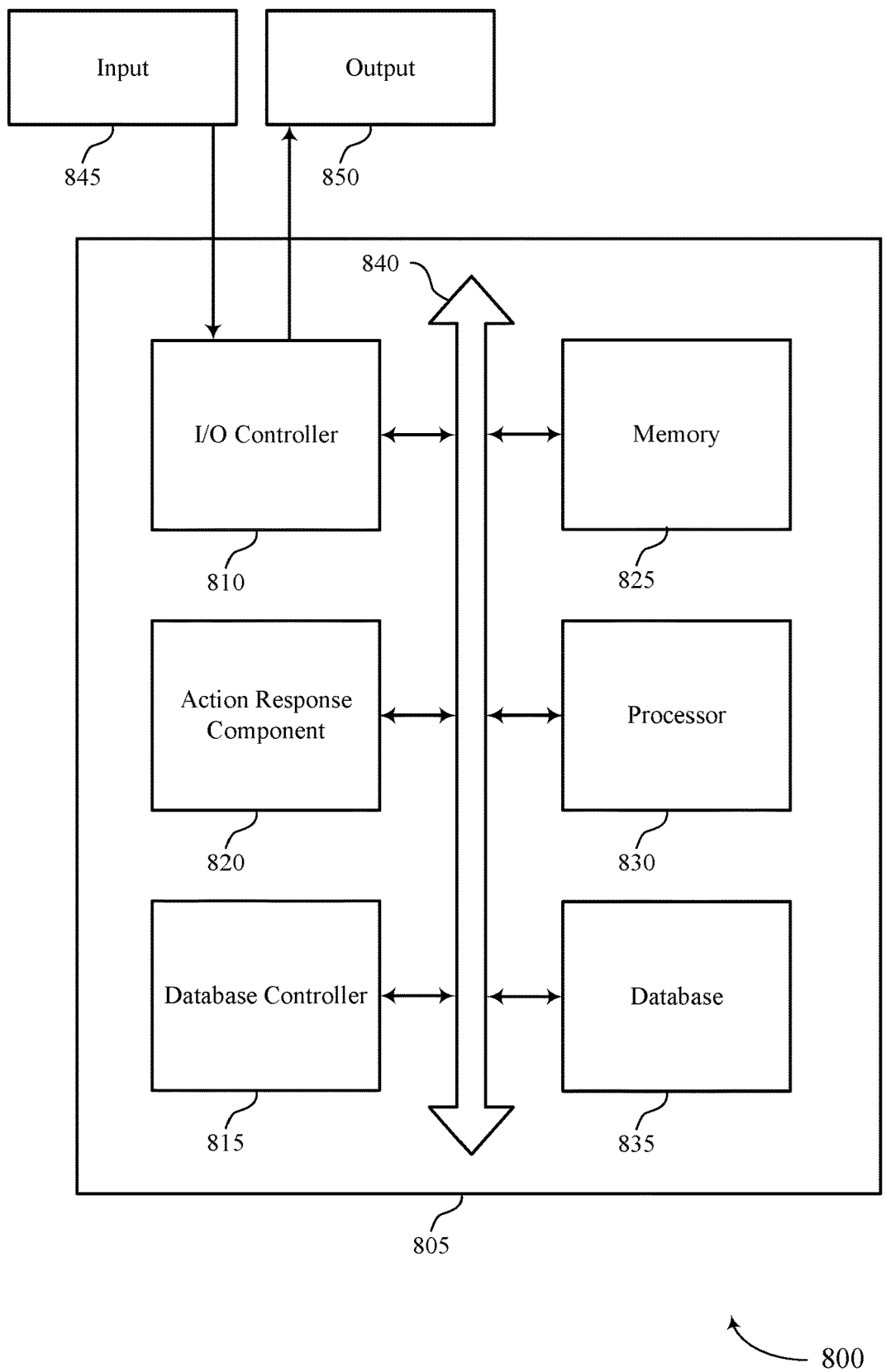
FIG. 8 illustrates a diagram of a system including a device that supports a heated body pillow in accordance with examples as disclosed herein.

FIG. 8 illustrates a diagram of a system 800 including a device 805 that supports a heated body pillow in accordance with examples as disclosed herein. The device 805 may be an example of or include the components of a device 505, a device 605, or a Body Pillow as described herein. The device 805 may include components for bi-directional voice and data communications including components for transmitting and receiving communications, such as an action response component 820, an I/O controller 810, a database controller 815, a memory 825, a processor 830, and a database 835. These components may be in electronic communication or otherwise coupled (e.g., operatively, communicatively, functionally, electronically, electrically) via one or more buses (e.g., a bus 840).

The I/O controller 810 may manage input signals 845 and output signals 850 for the device 805. The I/O controller 810 may also manage peripherals not integrated into the device 805. In some cases, the I/O controller 810 may represent a physical connection or port to an external peripheral. In some cases, the I/O controller 810 may utilize an operating system such as iOS®, ANDROID®, MS-DOS®, MS-WINDOWS®, OS/2®, UNIX®, LINUX®, or another known operating system. Additionally or alternatively, the I/O controller 810 may represent or interact with a modem, a keyboard, a mouse, a touchscreen, or a similar device. In some cases, the I/O controller 810 may be implemented as part of a processor. In some examples, a user may interact with the device 805 via the I/O controller 810 or via hardware components controlled by the I/O controller 810.

The database controller 815 may manage data storage and processing in a database 835. The database 835 may be external to the device 805, temporarily or permanently connected to the device 805, or a data storage component of the device 805. In some cases, a user may interact with the database controller 815. In some other cases, the database controller 815 may operate automatically without user interaction. The database 835 may be an example of a persistent data store, a single database, a distributed database, multiple distributed databases, a database management system, or an emergency backup database.

Memory 825 may include random-access memory (RAM) and ROM. The memory 825 may store computer-readable, computer-executable software including instructions that, when executed, cause the processor to perform various functions described herein. In some cases, the memory 825 may contain, among other things, a BIOS which may control basic hardware or software operation such as the interaction with peripheral components or devices.

The processor 830 may include an intelligent hardware device (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 830 may be configured to operate a memory array using a memory controller. In some other cases, a memory controller may be integrated into the processor 830. The processor 830 may be configured to execute computer-readable instructions stored in memory 825 to perform various functions (e.g., functions or tasks supporting heated body pillow).

The action response component 820 may support operating a heated pillow in accordance with examples as disclosed herein. For example, the action response component 820 may be configured as or otherwise support a means for receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The action response component 820 may be configured as or otherwise support a means for adjusting the operating temperature of the heating element based at least in part on receiving the one or more commands.

By including or configuring the action response component 820 in accordance with examples as described herein, the device 805 may support techniques for [[*Add device-level advantages (e.g., improved communication reliability, reduced latency, improved user experience related to reduced processing, reduced power consumption, more efficient utilization of communication resources, improved coordination between devices, longer battery life, improved utilization of processing capability)*]]

Figure 9:
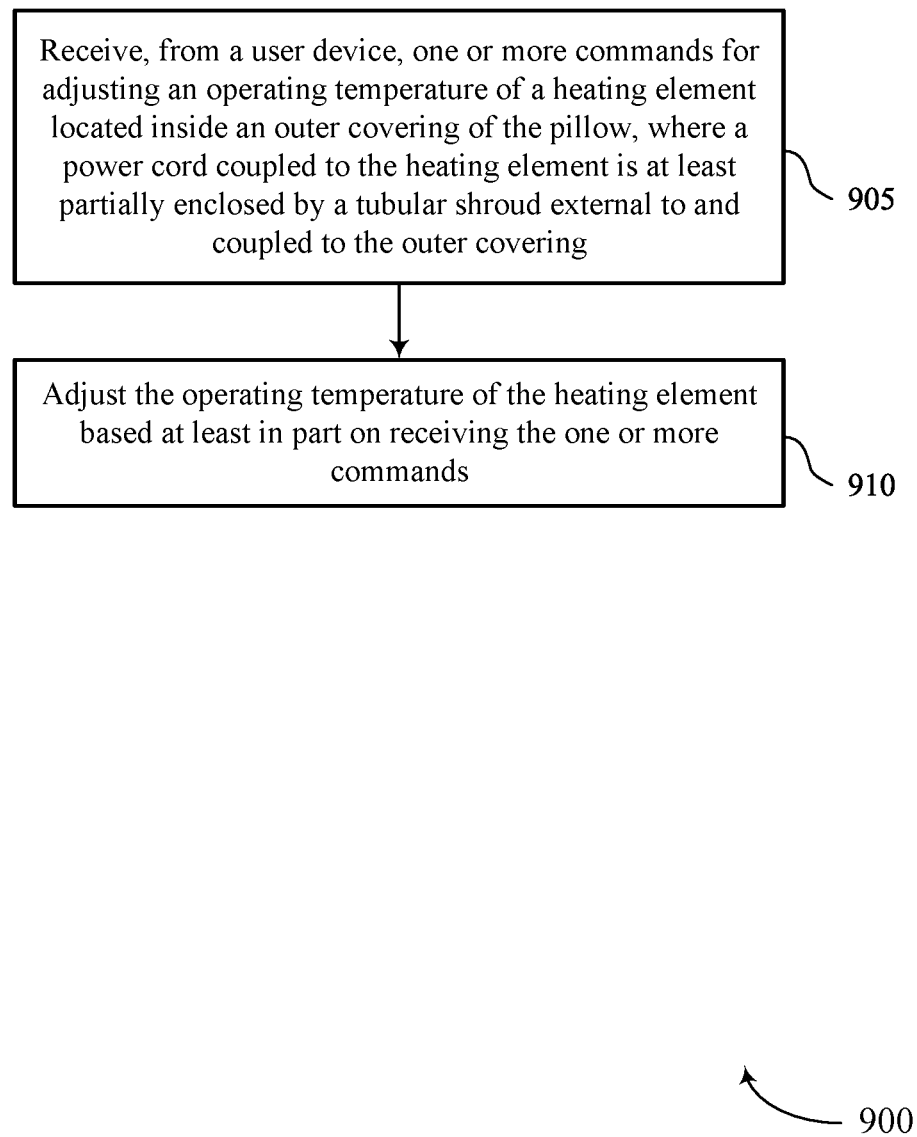
FIGS. 9 through 14 illustrate flowcharts showing methods that support a heated body pillow in accordance with examples as disclosed herein.

FIG. 9 illustrates a flowchart showing a method 900 that supports a heated body pillow in accordance with examples as disclosed herein. The operations of the method 900 may be implemented by a Body Pillow or its components as described herein. For example, the operations of the method 900 may be performed by a Body Pillow as described with reference to FIGS. 1 through 8. In some examples, a Body Pillow may execute a set of instructions to control the functional elements of the Body Pillow to perform the described functions. Additionally, or alternatively, the Body Pillow may perform aspects of the described functions using special-purpose hardware.

At 905, the method may include receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The operations of 905 may be performed in accordance with examples as disclosed herein. In some examples, aspects of the operations of 905 may be performed by a user device communication component 725 as described with reference to FIG. 7.

At 910, the method may include adjusting the operating temperature of the heating element based at least in part on receiving the one or more commands. The operations of 910 may be performed in accordance with examples as disclosed herein. In some examples, aspects of the operations of 910 may be performed by a heating element adjustment component 730 as described with reference to FIG. 7.

In some examples, an apparatus as described herein may perform a method or methods, such as the method 900. The apparatus may include features, circuitry, logic, means, or instructions (e.g., a non-transitory computer-readable medium storing instructions executable by a processor) for receiving, from a user device, one or more commands for adjusting an operating temperature of a heating element located inside an outer covering of the pillow, wherein a power cord coupled to the heating element is at least partially enclosed by a tubular shroud external to and coupled to the outer covering and adjusting the operating temperature of the heating element based at least in part on receiving the one or more commands.

Some examples of the method 900 and the apparatus described herein may further include operations, features, means, or instructions for receiving an indication of an operating temperature of a thermostat associated with a structure and wherein adjusting the operating temperature of the heating element may be based at least in part on receiving the indication of the operating temperature of the thermostat.

Some examples of the method 900 and the apparatus described herein may further include operations, features, means, or instructions for transmitting a thermostat temperature adjustment command based at least in part on adjusting the operating temperature of the heating element.

Some examples of the method 900 and the apparatus described herein may further include operations, features, means, or instructions for detecting, with a temperature sensor of the heated pillow, an ambient temperature of an environment in which the pillow may be located and wherein adjusting the operating temperature of the heating element may be based at least in part on the ambient temperature.

Some examples of the method 900 and the apparatus described herein may further include operations, features, means, or instructions for transmitting a thermostat temperature adjustment command based at least in part on the ambient temperature of the environment.

Some examples of the method 900 and the apparatus described herein may further include operations, features, means, or instructions for receiving the one or more commands comprises receiving a temperature adjustment schedule and adjusting the operating temperature of the heating element comprises adjusting the operating temperature of the heating temperature for a duration of the temperature adjustment schedule in accordance with the temperature adjustment schedule.

In some examples of the method 900 and the apparatus described herein, the temperature adjustment schedule indicates that the operating temperature of the heating element may be to be adjusted to a user-designated temperature at least a threshold amount of time before a user-designated point in time.

Some examples of the method 900 and the apparatus described herein may further include operations, features, means, or instructions for starting a shutoff timer based at least in part on a shutoff timer command, wherein receiving the one or more commands comprises receiving the shutoff timer command and deactivating the heating element based at least in part on an expiry of the shutoff timer.

Some examples of the method 900 and the apparatus described herein may further include operations, features, means, or instructions for receiving, from the user device, one or more second commands for adjusting a second operating temperature of a second heating element located inside an outer covering of the pillow, wherein the power cord may be coupled to the second heating element and adjusting the second operating temperature of the second heating element based at least in part on receiving the one or more second commands.

Some examples of the method 900 and the apparatus described herein may further include operations, features, means, or instructions for capturing, via a microphone of the pillow, audio in an environment in which the pillow may be located and transmitting the captured audio to the user device.

Some examples of the method 900 and the apparatus described herein may further include operations, features, means, or instructions for capturing, via a microphone of the pillow, audio in an environment in which the pillow may be located, identifying one or more spoken commands in the audio, and transmitting, via a local area network, one or more commands to one or more devices connected to the local area network based at least in part on the one or more spoken commands.

Some examples of the method 900 and the apparatus described herein may further include operations, features, means, or instructions for monitoring movement, sound, temperature, or any combination thereof of an environment in which the pillow may be located, determining one or more user sleep events based on the movement, sound, temperature, or any combination thereof, and transmitting, to a user device, a report indicating the one or more user sleep events.

In some examples of the method 900 and the apparatus described herein, playing, via a speaker of the pillow, an audible schedule reminder based at least in part on a user-specified event and a time at which the event may be to take place.

Some examples of the method 900 and the apparatus described herein may further include operations, features, means, or instructions for receiving, from a user device, an audio recording and playing, via a speaker of the pillow, the audio recording based at least in part on receiving a playback command from the user device.

Some examples of the method 900 and the apparatus described herein may further include operations, features, means, or instructions for receiving, from the user device, one or more third commands for adjusting a vibration strength of one or more vibrating elements located inside the outer covering of the pillow, adjusting the vibration strength of the one or more vibrating elements based at least in part on receiving the one or more third commands, and wherein the one or more vibrating elements vibrate in accordance with a user-specified vibration pattern.

In some examples of the method 900 and the apparatus described herein, the pillow further comprises a compartment that accepts a flexible, vented case that accepts and secures, at least partially within the case, an aromatic disk, an absorbent material that accepts an aromatic liquid, or both.

Some examples of the method 900 and the apparatus described herein may further include operations, features, means, or instructions for receiving, from the user device, one or more fourth commands for adjusting an operating speed of one or more fans coupled to the outer covering, adjusting the operating speed of the one or more fans based at least in part on receiving the one or more fourth commands, and wherein at least a portion of the outer covering may be perforated and the one or more fans direct airflow through the portion of the outer covering.

In some examples of the method 900 and the apparatus described herein, at least a portion of the outer covering, at least a portion of the tubular shroud, or both, comprise imitation fur.

Figure 10:
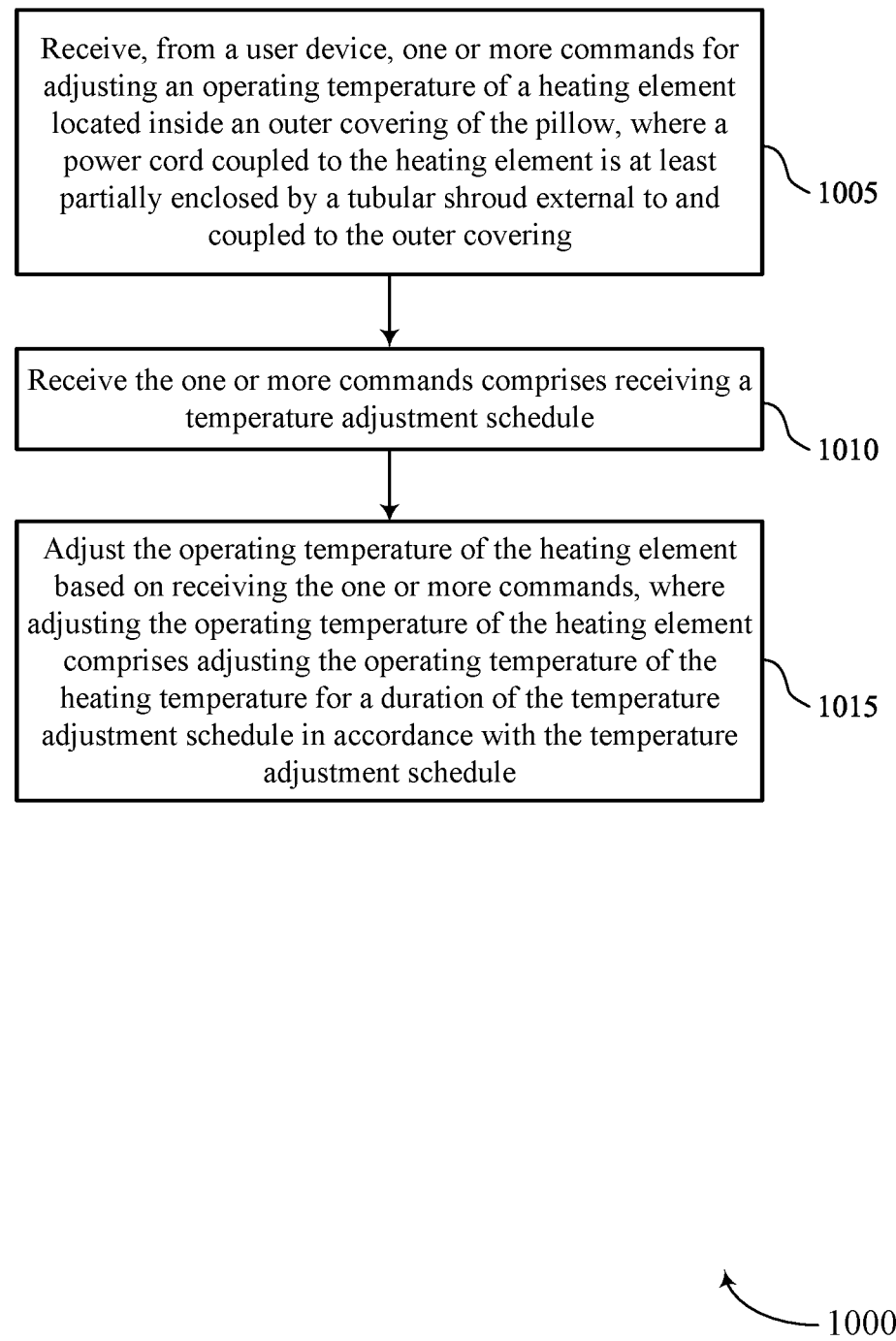

FIG. 10 illustrates a flowchart showing a method 1000 that supports a heated body pillow in accordance with examples as disclosed herein. The operations of the method 1000 may be implemented by a Body Pillow or its components as described herein. For example, the operations of the method 1000 may be performed by a Body Pillow as described with reference to FIGS. 1 through 8. In some examples, a Body Pillow may execute a set of instructions to control the functional elements of the Body Pillow to perform the described functions. Additionally, or alternatively, the Body Pillow may perform aspects of the described functions using special-purpose hardware.

At 1005, the method may include receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The operations of 1005 may be performed in accordance with examples as disclosed herein. In some examples, aspects of the operations of 1005 may be performed by a user device communication component 725 as described with reference to FIG. 7.

At 1010, the method may include receiving the one or more commands comprises receiving a temperature adjustment schedule. The operations of 1010 may be performed in accordance with examples as disclosed herein. In some examples, aspects of the operations of 1010 may be performed by a scheduling component 745 as described with reference to FIG. 7.

At 1015, the method may include adjusting the operating temperature of the heating element based at least in part on receiving the one or more commands, where adjusting the operating temperature of the heating element includes adjusting the operating temperature of the heating temperature for a duration of the temperature adjustment schedule in accordance with the temperature adjustment schedule. The operations of 1015 may be performed in accordance with examples as disclosed herein. In some examples, aspects of the operations of 1015 may be performed by a heating element adjustment component 730 as described with reference to FIG. 7.

Figure 11:
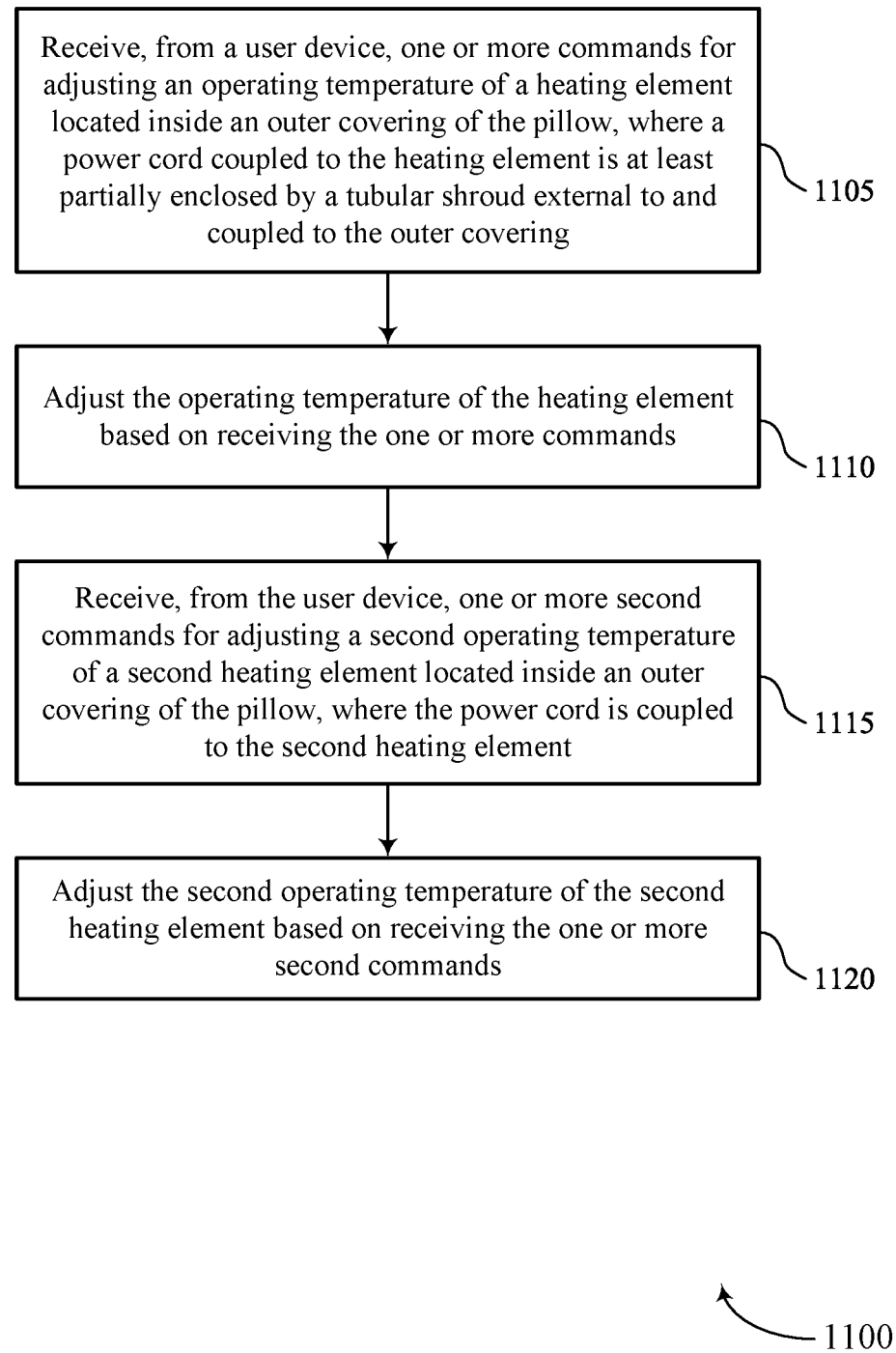

FIG. 11 illustrates a flowchart showing a method 1100 that supports a heated body pillow in accordance with examples as disclosed herein. The operations of the method 1100 may be implemented by a Body Pillow or its components as described herein. For example, the operations of the method 1100 may be performed by a Body Pillow as described with reference to FIGS. 1 through 8. In some examples, a Body Pillow may execute a set of instructions to control the functional elements of the Body Pillow to perform the described functions. Additionally, or alternatively, the Body Pillow may perform aspects of the described functions using special-purpose hardware.

At 1105, the method may include receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The operations of 1105 may be performed in accordance with examples as disclosed herein. In some examples, aspects of the operations of 1105 may be performed by a user device communication component 725 as described with reference to FIG. 7.

At 1110, the method may include adjusting the operating temperature of the heating element based at least in part on receiving the one or more commands. The operations of 1110 may be performed in accordance with examples as disclosed herein. In some examples, aspects of the operations of 1110 may be performed by a heating element adjustment component 730 as described with reference to FIG. 7.

At 1115, the method may include receiving, from the user device, one or more second commands for adjusting a second operating temperature of a second heating element located inside an outer covering of the pillow, wherein the power cord is coupled to the second heating element. The operations of 1115 may be performed in accordance with examples as disclosed herein. In some examples, aspects of the operations of 1115 may be performed by a user device communication component 725 as described with reference to FIG. 7.

At 1120, the method may include adjusting the second operating temperature of the second heating element based at least in part on receiving the one or more second commands. The operations of 1120 may be performed in accordance with examples as disclosed herein. In some examples, aspects of the operations of 1120 may be performed by a heating element adjustment component 730 as described with reference to FIG. 7.

Figure 12:
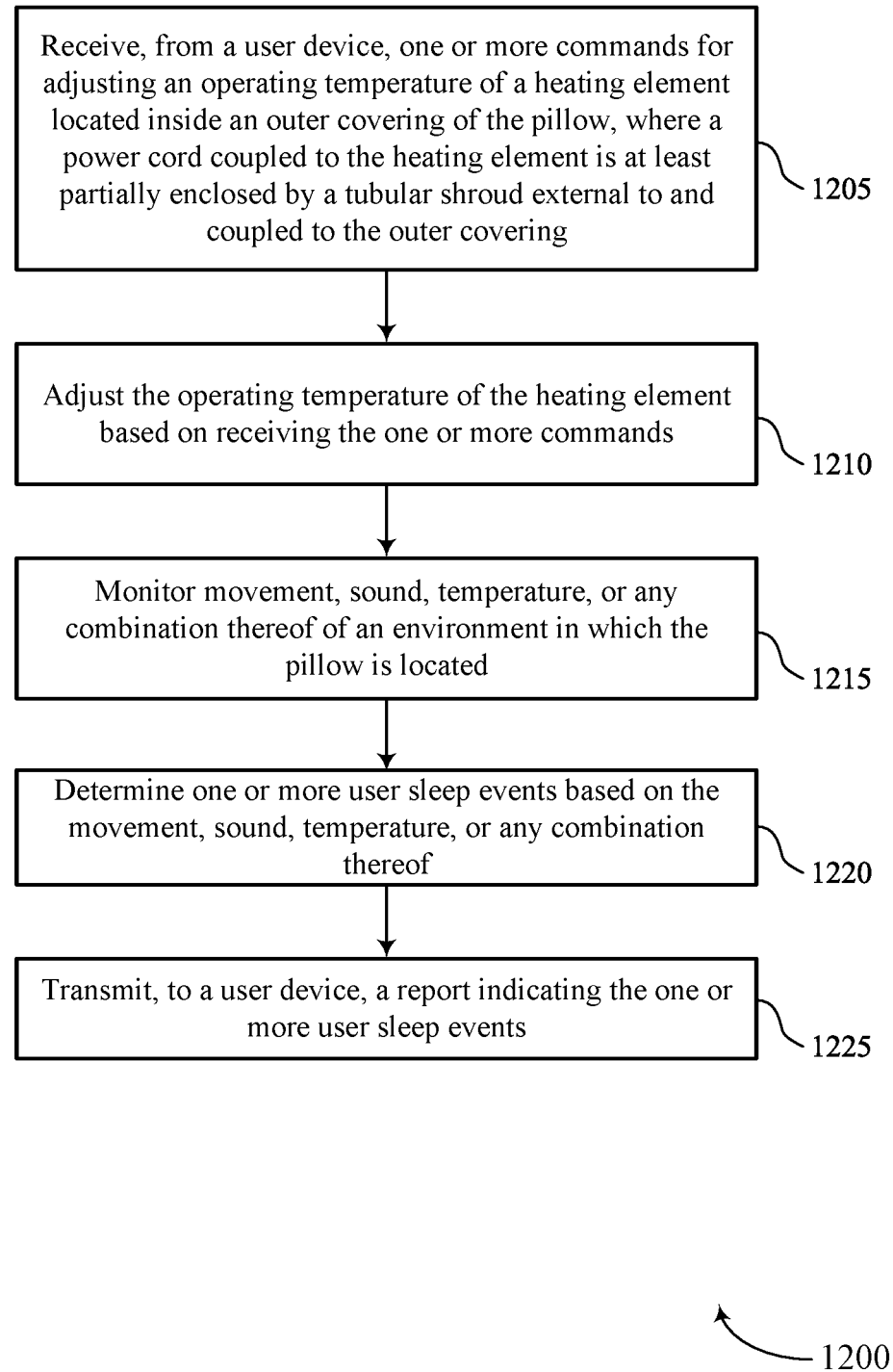

FIG. 12 illustrates a flowchart showing a method 1200 that supports a heated body pillow in accordance with examples as disclosed herein. The operations of the method 1200 may be implemented by a Body Pillow or its components as described herein. For example, the operations of the method 1200 may be performed by a Body Pillow as described with reference to FIGS. 1 through 8. In some examples, a Body Pillow may execute a set of instructions to control the functional elements of the Body Pillow to perform the described functions. Additionally, or alternatively, the Body Pillow may perform aspects of the described functions using special-purpose hardware.

At 1205, the method may include receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The operations of 1205 may be performed in accordance with examples as disclosed herein. In some examples, aspects of the operations of 1205 may be performed by a user device communication component 725 as described with reference to FIG. 7.

At 1210, the method may include adjusting the operating temperature of the heating element based at least in part on receiving the one or more commands. The operations of 1210 may be performed in accordance with examples as disclosed herein. In some examples, aspects of the operations of 1210 may be performed by a heating element adjustment component 730 as described with reference to FIG. 7.

At 1215, the method may include monitoring movement, sound, temperature, or any combination thereof of an environment in which the pillow is located. The operations of 1215 may be performed in accordance with examples as disclosed herein. In some examples, aspects of the operations of 1215 may be performed by a sleep monitoring component 760 as described with reference to FIG. 7.

At 1220, the method may include determining one or more user sleep events based on the movement, sound, temperature, or any combination thereof. The operations of 1220 may be performed in accordance with examples as disclosed herein. In some examples, aspects of the operations of 1220 may be performed by a sleep monitoring component 760 as described with reference to FIG. 7.

At 1225, the method may include transmitting, to a user device, a report indicating the one or more user sleep events. The operations of 1225 may be performed in accordance with examples as disclosed herein. In some examples, aspects of the operations of 1225 may be performed by a user device communication component 725 as described with reference to FIG. 7.

Figure 13:
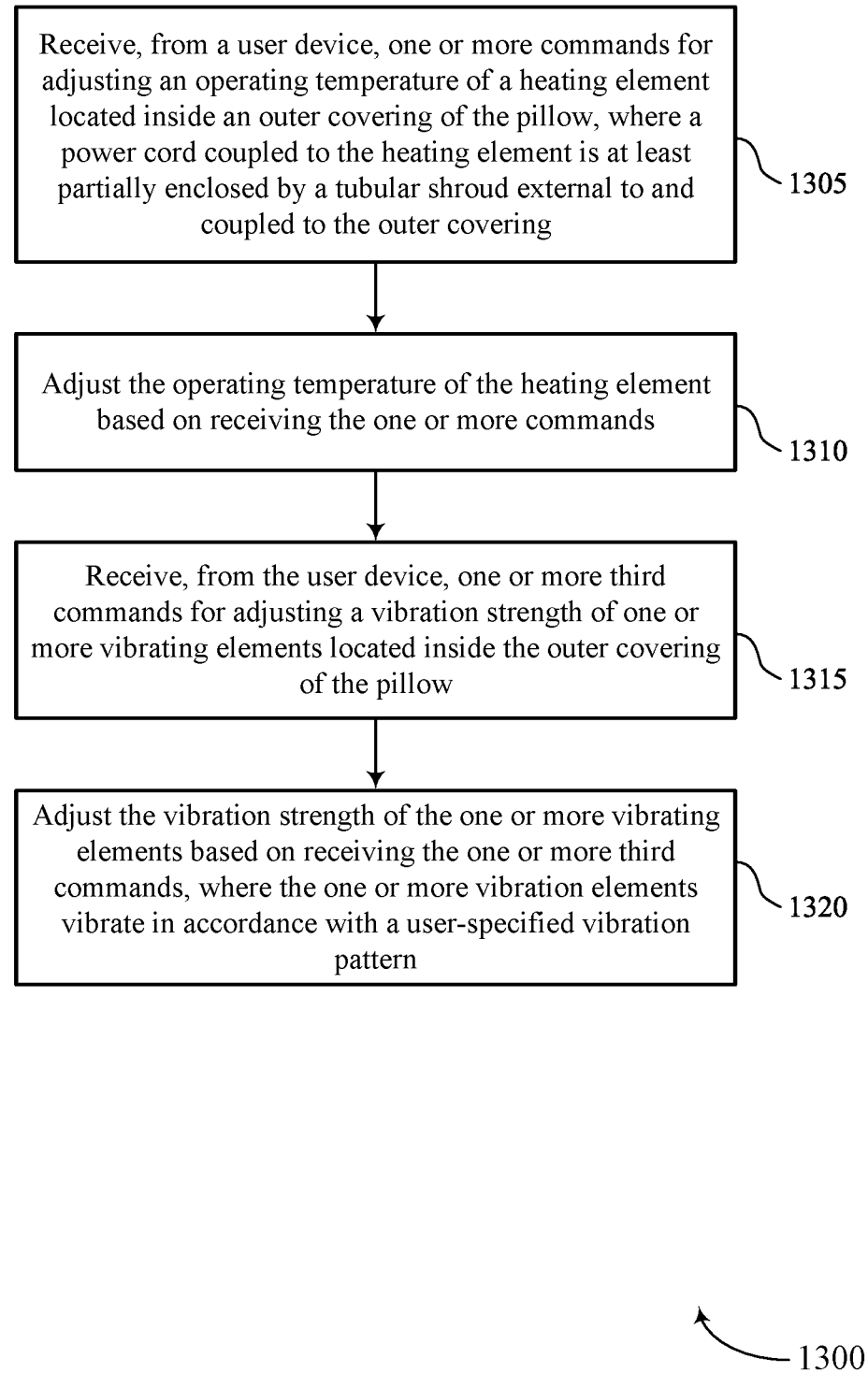

FIG. 13 illustrates a flowchart showing a method 1300 that supports a heated body pillow in accordance with examples as disclosed herein. The operations of the method 1300 may be implemented by a Body Pillow or its components as described herein. For example, the operations of the method 1300 may be performed by a Body Pillow as described with reference to FIGS. 1 through 8. In some examples, a Body Pillow may execute a set of instructions to control the functional elements of the Body Pillow to perform the described functions. Additionally, or alternatively, the Body Pillow may perform aspects of the described functions using special-purpose hardware.

At 1305, the method may include receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The operations of 1305 may be performed in accordance with examples as disclosed herein. In some examples, aspects of the operations of 1305 may be performed by a user device communication component 725 as described with reference to FIG. 7.

At 1310, the method may include adjusting the operating temperature of the heating element based at least in part on receiving the one or more commands. The operations of 1310 may be performed in accordance with examples as disclosed herein. In some examples, aspects of the operations of 1310 may be performed by a heating element adjustment component 730 as described with reference to FIG. 7.

At 1315, the method may include receiving, from the user device, one or more third commands for adjusting a vibration strength of one or more vibrating elements located inside the outer covering of the pillow. The operations of 1315 may be performed in accordance with examples as disclosed herein. In some examples, aspects of the operations of 1315 may be performed by a user device communication component 725 as described with reference to FIG. 7.

At 1320, the method may include adjusting the vibration strength of the one or more vibrating elements based at least in part on receiving the one or more third commands, wherein the one or more vibrating elements vibrate in accordance with a user-specified vibration pattern. The operations of 1320 may be performed in accordance with examples as disclosed herein. In some examples, aspects of the operations of 1320 may be performed by a vibration component 765 as described with reference to FIG. 7.

Figure 14:
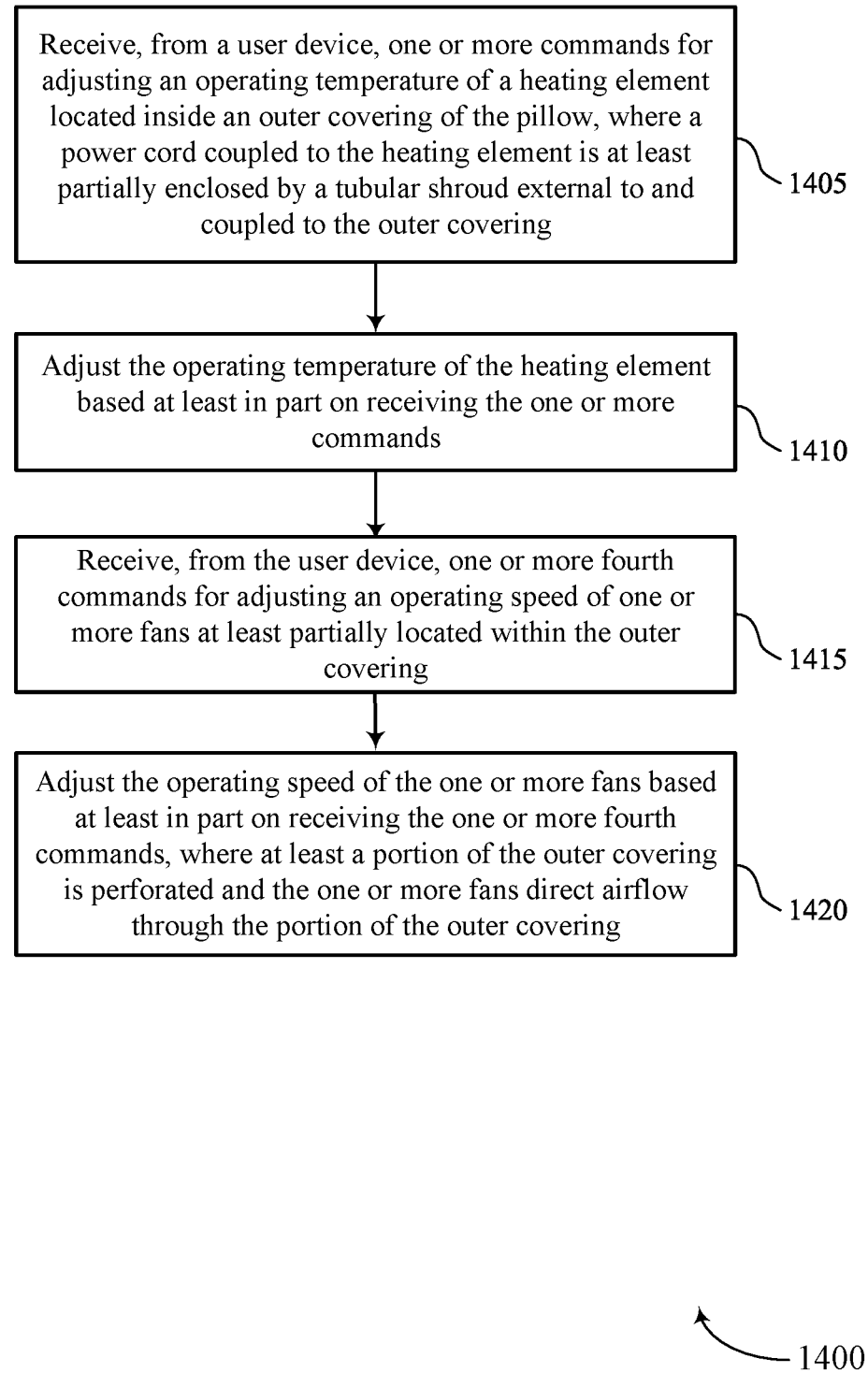

FIG. 14 illustrates a flowchart showing a method 1400 that supports a heated body pillow in accordance with examples as disclosed herein. The operations of the method 1400 may be implemented by a Body Pillow or its components as described herein. For example, the operations of the method 1400 may be performed by a Body Pillow as described with reference to FIGS. 1 through 8. In some examples, a Body Pillow may execute a set of instructions to control the functional elements of the Body Pillow to perform the described functions. Additionally, or alternatively, the Body Pillow may perform aspects of the described functions using special-purpose hardware.

At 1405, the method may include receiving, from a user device, one or more commands for adjusting an operating temperature of a heating element located inside an outer covering of the pillow, wherein a power cord coupled to the heating element is at least partially enclosed by a tubular shroud external to and coupled to the outer covering. The operations of 1405 may be performed in accordance with examples as disclosed herein. In some examples, aspects of the operations of 1405 may be performed by a user device communication component 725 as described with reference to FIG. 7.

At 1410, the method may include adjusting the operating temperature of the heating element based at least in part on receiving the one or more commands. The operations of 1410 may be performed in accordance with examples as disclosed herein. In some examples, aspects of the operations of 1410 may be performed by a heating element adjustment component 730 as described with reference to FIG. 7.

At 1415, the method may include receiving, from the user device, one or more fourth commands for adjusting an operating speed of one or more fans coupled to the outer covering. The operations of 1415 may be performed in accordance with examples as disclosed herein. In some examples, aspects of the operations of 1415 may be performed by a user device communication component 725 as described with reference to FIG. 7.

At 1420, the method may include adjusting the operating speed of the one or more fans based at least in part on receiving the one or more fourth commands, wherein at least a portion of the outer covering is perforated and the one or more fans direct airflow through the portion of the outer covering. The operations of 1420 may be performed in accordance with examples as disclosed herein. In some examples, aspects of the operations of 1420 may be performed by a cooling component 770 as described with reference to FIG. 7.

The following provides an overview of aspects of the present disclosure:

Aspect 1: A method for operating a heated pillow, comprising: receiving, from a user device, one or more commands for adjusting an operating temperature of a heating element located inside an outer covering of the pillow, wherein a power cord coupled to the heating element is at least partially enclosed by a tubular shroud external to and coupled to the outer covering; and adjusting the operating temperature of the heating element based at least in part on receiving the one or more commands.

Aspect 2: The method of aspect 1, further comprising: receiving an indication of an operating temperature of a thermostat associated with a structure; and wherein adjusting the operating temperature of the heating element is based at least in part on receiving the indication of the operating temperature of the thermostat.

Aspect 3: The method of any of aspects 1 through 2, further comprising: transmitting a thermostat temperature adjustment command based at least in part on adjusting the operating temperature of the heating element.

Aspect 4: The method of any of aspects 1 through 3, further comprising: detecting, with a temperature sensor of the pillow, an ambient temperature of an environment in which the pillow is located; wherein adjusting the operating temperature of the heating element is based at least in part on the ambient temperature.

Aspect 5: The method of aspect 4, further comprising: transmitting a thermostat temperature adjustment command based at least in part on the ambient temperature of the environment.

Aspect 6: The method of any of aspects 1 through 5, wherein receiving the one or more commands comprises receiving a temperature adjustment schedule; and adjusting the operating temperature of the heating element comprises adjusting the operating temperature of the heating temperature for a duration of the temperature adjustment schedule in accordance with the temperature adjustment schedule.

Aspect 7: The method of aspect 6, wherein the temperature adjustment schedule indicates that the operating temperature of the heating element is to be adjusted to a user-designated temperature at least a threshold amount of time before a user-designated point in time.

Aspect 8: The method of any of aspects 1 through 7, further comprising: starting a shutoff timer based at least in part on a shutoff timer command, wherein receiving the one or more commands comprises receiving the shutoff timer command; and deactivating the heating element based at least in part on an expiry of the shutoff timer.

Aspect 9: The method of any of aspects 1 through 8, further comprising: receiving, from the user device, one or more second commands for adjusting a second operating temperature of a second heating element located inside an outer covering of the pillow, wherein the power cord is coupled to the second heating element; and adjusting the second operating temperature of the second heating element based at least in part on receiving the one or more second commands.

Aspect 10: The method of any of aspects 1 through 9, further comprising: capturing, via a microphone of the pillow, audio in an environment in which the pillow is located; transmitting the captured audio to the user device.

Aspect 11: The method of any of aspects 1 through 10, further comprising: capturing, via a microphone of the pillow, audio in an environment in which the pillow is located; identifying one or more spoken commands in the audio; and transmitting, via a local area network, one or more commands to one or more devices connected to the local area network based at least in part on the one or more spoken commands.

Aspect 12: The method of any of aspects 1 through 11, further comprising: monitoring movement, sound, temperature, or any combination thereof of an environment in which the pillow is located; determining one or more user sleep events based on the movement, sound, temperature, or any combination thereof; and transmitting, to the user device, a report indicating the one or more user sleep events.

Aspect 13: The method of any of aspects 1 through 12, further comprising: playing, via a speaker of the pillow, an audible schedule reminder based at least in part on a user-specified event and a time at which the event is to take place.

Aspect 14: The method of any of aspects 1 through 13, further comprising: receiving, from the user device, an audio recording; playing, via a speaker of the pillow, the audio recording based at least in part on receiving a playback command from the user device.

Aspect 15: The method of any of aspects 1 through 14, further comprising: receiving, from the user device, one or more third commands for adjusting a vibration strength of one or more vibrating elements located inside the outer covering of the pillow; and adjusting the vibration strength of the one or more vibrating elements based at least in part on receiving the one or more third commands; wherein the one or more vibrating elements vibrate in accordance with a user-specified vibration pattern.

Aspect 16: The method of any of aspects 1 through 15, wherein the pillow further comprises a compartment that accepts a flexible, vented case that accepts and secures, at least partially within the case, an aromatic disk, an absorbent material that accepts an aromatic liquid, or both.

Aspect 17: The method of any of aspects 1 through 16, further comprising: receiving, from the user device, one or more fourth commands for adjusting an operating speed of one or more fans coupled to the outer covering; and adjusting the operating speed of the one or more fans based at least in part on receiving the one or more fourth commands; wherein at least a portion of the outer covering is perforated and the one or more fans direct airflow through the portion of the outer covering.

Aspect 18: The method of any of aspects 1 through 17, wherein at least a portion of the outer covering, at least a portion of the tubular shroud, or both, comprise imitation fur.

Aspect 19: An apparatus for operating a heated pillow, comprising a processor; memory coupled with the processor; and instructions stored in the memory and executable by the processor to cause the apparatus to perform a method of any of aspects 1 through 18.

Aspect 20: An apparatus for operating a heated pillow, comprising at least one means for performing a method of any of aspects 1 through 18.

Aspect 21: A non-transitory computer-readable medium storing code for operating a heated pillow, the code comprising instructions executable by a processor to perform a method of any of aspects 1 through 18.

It should be noted that these methods describe examples of implementations, and that the operations and the steps may be rearranged or otherwise modified such that other implementations are possible. In some examples, aspects from two or more of the methods may be combined. For example, aspects of each of the methods may include steps or aspects of the other methods, or other steps or techniques described herein. Thus, aspects of the disclosure may provide for consumer preference and maintenance interface.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

Information and signals described herein may be represented using any of a variety of different technologies and techniques. For example, data, instructions, commands, information, signals, bits, and symbols that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

As used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for operating a large body pillow, comprising:
   receiving, from a user device, one or more commands for adjusting an operating temperature of multiple electrical heating element located inside an outer covering of the large body pillow, said large body pillow, wherein a power cord coupled to the multiple heating elements are at least partially enclosed by a tubular shroud external to and coupled to the outer covering;
   adjusting the operating temperature of the multiple heating element based at least in part on receiving the one or more commands using a wireless connection from the user device;
   receiving an indication of a second operating temperature of a smart thermostat associated with a structure at a processor within the large body pillow;
   wherein adjusting the operating temperature of the electrical heating element is based at least in part on receiving the indication of the second operating temperature of the smart thermostat;
   wherein the pillow processor adjust the operating temperature of the large body pillow based on a configuration of the smart thermostat with the large body pillow transmitting a first command to the smart thermostat to lower the second operating temperature of a structure heating system associated with the smart thermostat to reduce energy consumption by the structure heating system.

2. The method of claim 1, further comprising:
   adjusting multiple vibrating elements within the heated body pillow using the user device to adjust vibrations and provide vibration sensations to different parts of a user's body according to at least one generated vibration pattern.

3. The method of claim 1, further comprising:
   transmitting a thermostat temperature adjustment command based at least in part on adjusting the operating temperature of the heating element.

4. The method of claim 1, further comprising:
   detecting, with a temperature sensor of the pillow, an ambient temperature of an environment in which the pillow is located;
   wherein adjusting the operating temperature of the electrical heating element is based at least in part on the ambient temperature.

5. The method of claim 4, further comprising:
   transmitting a thermostat temperature adjustment command based at least in part on the ambient temperature of the environment.

6. The method of claim 1, wherein:
   receiving the one or more commands comprises receiving a temperature adjustment schedule; and
   adjusting the operating temperature of the electrical heating element comprises adjusting the operating temperature of the electrical heating element for a duration of the temperature adjustment schedule in accordance with the temperature adjustment schedule.

7. The method of claim 6, wherein the temperature adjustment schedule indicates that the operating temperature of the electrical heating element is to be adjusted to a user-designated temperature at least a threshold amount of time before a user-designated point in time.

8. The method of claim 1, further comprising:
   starting a shutoff timer based at least in part on a shutoff timer command, wherein receiving the one or more commands comprises receiving the shutoff timer command; and
   deactivating the electrical heating element based at least in part on an expiry of the shutoff timer.

9. The method of claim 1, further comprising:
   receiving, from the user device, one or more second commands for adjusting a second operating temperature of a second electrical heating element located inside an outer covering of the pillow, wherein the power cord is coupled to the second electrical heating element; and adjusting the second operating temperature of the second electrical heating element based at least in part on receiving the one or more second commands.

10. The method of claim 1, further comprising:
capturing, via a microphone of the pillow, audio in an environment in which the pillow is located; and
transmitting the captured audio to the user device.

11. The method of claim 1, further comprising:
capturing, via a microphone of the pillow, audio in an environment in which the pillow is located;
identifying one or more spoken commands in the audio; and
transmitting, via a local area network, one or more commands to one or more devices connected to the local area network based at least in part on the one or more spoken commands.

12. The method of claim 1, further comprising:
monitoring movement, sound, temperature, or any combination thereof of an environment in which the pillow is located;
determining one or more user sleep events based on the movement, sound, temperature, or any combination thereof; and
transmitting, to the user device, a report indicating the one or more user sleep events.

13. The method of claim 1, further comprising:
playing, via a speaker of the pillow, an audible schedule reminder based at least in part on a user-specified event and a time at which the user-specified event is to take place.

14. The method of claim 1, further comprising:
receiving, from the user device, an audio recording; and
playing, via a speaker of the pillow, the audio recording based at least in part on receiving a playback command from the user device.

15. The method of claim 1, further comprising:
receiving, from the user device, one or more third commands for adjusting a vibration strength of one or more vibrating elements located inside the outer covering of the pillow; and
adjusting the vibration strength of the one or more vibrating elements based at least in part on receiving the one or more third commands;
wherein the one or more vibrating elements vibrate in accordance with a user-specified vibration pattern.

16. The method of claim 1, wherein the pillow further comprises a compartment that accepts a flexible, vented case that accepts and secures, at least partially within the case, an aromatic disk, an absorbent material that accepts an aromatic liquid, or both.

17. The method of claim 1, further comprising:
receiving, from the user device, one or more fourth commands for adjusting an operating speed of one or more fans coupled to the outer covering; and
adjusting the operating speed of the one or more fans based at least in part on receiving the one or more fourth commands;
wherein at least a portion of the outer covering is perforated and the one or more fans direct airflow through the portion of the outer covering.

18. The method of claim 1, wherein at least a portion of the outer covering, at least a portion of the tubular shroud, or both, comprise imitation fur.

19. A heated body pillow, comprising:
a processor;
memory coupled with the processor; and
instructions stored in the memory and executable by the processor to cause the pillow to:
receive, from a user device, one or more commands for adjusting an operating temperature of multiple electrical heating elements located inside an outer covering of the pillow, wherein a power cord coupled to the electrical heating element is at least partially enclosed by a tubular shroud external to and coupled to the outer covering;
adjust the operating temperature of the multiple electrical heating elements based at least in part on receiving the one or more commands using a wireless connection from the user device;
receiving an indication of a second operating temperature of a smart thermostat associated with a structure at the processor;
wherein adjusting the operating temperature of the electrical heating element is based at least in part on receiving the indication of the second operating temperature of the smart thermostat;
wherein the pillow processor adjust the operating temperature of the large body pillow based on a configuration of the smart thermostat with the large body pillow transmitting a first command to the smart thermostat to lower the second operating temperature of a structure heating system associated with the smart thermostat to reduce energy consumption by the structure heating system.

20. A non-transitory computer-readable medium storing code, the code comprising instructions executable by a processor embedded in a body pillow to:
receive, from a user device, one or more commands for adjusting an operating temperature of a plurality of electrical heating element located inside an outer covering of a body pillow, wherein a power cord coupled to the electrical heating elements is at least partially enclosed by a tubular shroud external to and coupled to the outer covering;
adjust the operating temperature of the electrical heating elements based at least in part on receiving the one or more commands;
adjusting multiple vibrating elements within the heated body pillow using the user device to adjust vibrations and provide vibration sensations to different parts of a user's body according to at least one generated vibration pattern;
receiving an indication of a second operating temperature of a smart thermostat associated with a structure at the processor;
wherein adjusting the operating temperature of the electrical heating element is based at least in part on receiving the indication of the second operating temperature of the smart thermostat;
wherein the pillow processor adjust the operating temperature of the large body pillow based on a configuration of the smart thermostat with the large body pillow transmitting a first command to the smart thermostat to lower the second operating temperature of a structure heating system associated with the smart thermostat to reduce energy consumption by the structure heating system.

* * * * *